US012076177B2

(12) United States Patent
Kunio

(10) Patent No.: US 12,076,177 B2
(45) Date of Patent: Sep. 3, 2024

(54) APPARATUSES, SYSTEMS, METHODS AND STORAGE MEDIUMS FOR PERFORMANCE OF CO-REGISTRATION

(71) Applicant: CANON U.S.A., INC., Melville, NY (US)

(72) Inventor: Mie Kunio, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 436 days.

(21) Appl. No.: 17/427,052

(22) PCT Filed: Jan. 28, 2020

(86) PCT No.: PCT/US2020/015403
§ 371 (c)(1),
(2) Date: Jul. 29, 2021

(87) PCT Pub. No.: WO2020/159984
PCT Pub. Date: Aug. 6, 2020

(65) Prior Publication Data
US 2022/0104786 A1    Apr. 7, 2022

Related U.S. Application Data

(60) Provisional application No. 62/798,885, filed on Jan. 30, 2019.

(51) Int. Cl.
*A61B 6/00*    (2006.01)
*A61B 5/318*   (2021.01)
(Continued)

(52) U.S. Cl.
CPC ............ *A61B 6/5247* (2013.01); *A61B 5/318* (2021.01); *A61B 6/12* (2013.01); *A61B 6/463* (2013.01);
(Continued)

(58) Field of Classification Search
CPC ......... A61B 6/5247; A61B 5/318; A61B 6/12; A61B 6/463; A61B 6/481; A61B 6/504;
(Continued)

(56) References Cited

U.S. PATENT DOCUMENTS 5,357,550 A    10/1994  Asahina et al.
6,341,036 B1    1/2002  Tearney et al.
(Continued)

FOREIGN PATENT DOCUMENTS

AU    2015/204201 B2    7/2016
JP    2013-56113 A      3/2013
(Continued)

OTHER PUBLICATIONS

Notification of Transmittal of the International Search Report and the Written Opinion of the ISA, and International Search Report and Written Opinion, for PCT/US2020/015403, dated Jun. 12, 2020.
(Continued)

*Primary Examiner* — Dhaval V Patel
(74) *Attorney, Agent, or Firm* — Canon U.S.A., Inc. IP Division

(57) ABSTRACT

One or more devices, systems, methods and storage mediums for optical imaging medical devices, such as, but not limited to, intravascular ultrasound (IVUS), Optical Coherence Tomography (OCT) and/or multi-modal OCT apparatuses and systems, and methods and storage mediums for use with same, for performing coregistration and/or selecting a co-registration algorithm are provided herein. One or more embodiments may involve using an image frame, such as, but not limited to, an angiography image frame, to display an imaging catheter path and calculate a reliability of co-registration between multiple imaging modalities. In one or more embodiments, coregistration feature(s) may be available in any image acquisition option(s), such as, but not
(Continued)

limited to, any angiography image acquisition option(s), and coregistration may be performed even in a case where a user finishes an imaging pullback, such as, but not limited to, an intravascular imaging pullback.

27 Claims, 25 Drawing Sheets

(51) Int. Cl.

| | |
|---|---|
| *A61B 6/12* | (2006.01) |
| *A61B 6/46* | (2024.01) |
| *A61B 6/50* | (2024.01) |
| *G06T 7/33* | (2017.01) |
| *A61B 5/00* | (2006.01) |
| *A61B 8/12* | (2006.01) |

(52) U.S. Cl.
CPC .............. *A61B 6/481* (2013.01); *A61B 6/504* (2013.01); *G06T 7/337* (2017.01); *A61B 5/0066* (2013.01); *A61B 6/467* (2013.01); *A61B 8/12* (2013.01); *G06T 2207/30101* (2013.01); *G06T 2207/30204* (2013.01)

(58) Field of Classification Search
CPC ......... A61B 5/0066; A61B 6/467; A61B 8/12; A61B 6/5235; A61B 8/5261; A61B 2576/02; A61B 5/0035; A61B 5/0084; A61B 5/7285; A61B 8/0883; A61B 8/0891; G06T 7/337; G06T 2207/30101; G06T 2207/30204; G06T 2207/10116; G06T 7/38

See application file for complete search history.

(56) References Cited

U.S. PATENT DOCUMENTS

| | | | |
|---|---|---|---|
| 6,763,261 B2 | 7/2004 | Casscells, III et al. | |
| 7,366,376 B2 | 4/2008 | Shishkov et al. | |
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,843,572 B2 | 11/2010 | Tearney et al. | |
| 7,859,679 B2 | 12/2010 | Bouma et al. | |
| 7,872,759 B2 | 1/2011 | Tearney et al. | |
| 7,889,348 B2 | 2/2011 | Tearney et al. | |
| 7,978,916 B2 | 7/2011 | Klingensmith et al. | |
| 8,045,177 B2 | 10/2011 | Tearney et al. | |
| 8,145,018 B2 | 3/2012 | Shishkov et al. | |
| 8,175,684 B2 | 5/2012 | Vaillant et al. | |
| 8,289,522 B2 | 10/2012 | Tearney et al. | |
| 8,478,387 B2 | 7/2013 | Xu | |
| 8,565,859 B2 | 10/2013 | Wang et al. | |
| 8,676,013 B2 | 3/2014 | Bouma et al. | |
| 8,838,213 B2 | 9/2014 | Tearney et al. | |
| 8,909,323 B2 | 12/2014 | Baumgart | |
| 8,928,889 B2 | 1/2015 | Tearney et al. | |
| RE45,534 E | 6/2015 | Huennekens et al. | |
| 9,087,368 B2 | 7/2015 | Tearney et al. | |
| 9,121,926 B2 | 9/2015 | Nair et al. | |
| 9,138,147 B2 | 9/2015 | Schmitt et al. | |
| 9,254,089 B2 | 2/2016 | Tearney et al. | |
| 9,286,673 B2 | 3/2016 | Begin et al. | |
| 9,292,918 B2 | 3/2016 | Zagrodsky et al. | |
| 9,295,391 B1 | 3/2016 | Tearney et al. | |
| 9,295,450 B2 | 3/2016 | Furuichi et al. | |
| 9,301,687 B2 | 4/2016 | Kemp | |
| 9,307,926 B2 | 4/2016 | Begin et al. | |
| 9,332,942 B2 | 5/2016 | Jaffer et al. | |
| 9,351,698 B2 | 5/2016 | Dascal et al. | |
| 9,415,550 B2 | 8/2016 | Tearney et al. | |
| 9,462,950 B2 | 10/2016 | Xu | |
| 9,557,154 B2 | 1/2017 | Tearney et al. | |
| 9,833,221 B2 | 12/2017 | Hutchins et al. | |
| 9,901,317 B2 | 2/2018 | Shimamura et al. | |
| 10,485,632 B1* | 11/2019 | Al-Ekrish | A61B 90/39 |
| 11,364,005 B2* | 6/2022 | Smith | A61B 6/502 |
| 2010/0092389 A1 | 4/2010 | Jaffer | |
| 2010/0208957 A1 | 8/2010 | Chen et al. | |
| 2011/0292400 A1 | 12/2011 | Fleming et al. | |
| 2012/0101374 A1 | 4/2012 | Tearney et al. | |
| 2014/0275996 A1* | 9/2014 | Stigall | A61B 6/5247 |
| | | | 600/424 |
| 2014/0276011 A1 | 9/2014 | Schmitt et al. | |
| 2015/0131886 A1 | 5/2015 | Aben et al. | |
| 2015/0250438 A1 | 9/2015 | Bozkaya et al. | |
| 2015/0272442 A1 | 10/2015 | Motafakker-Fard et al. | |
| 2016/0171711 A1 | 6/2016 | Gopinath et al. | |
| 2016/0206267 A1 | 7/2016 | Shimizu et al. | |
| 2016/0228097 A1 | 8/2016 | Jaffer et al. | |
| 2016/0335766 A1 | 11/2016 | Ambwani et al. | |
| 2016/0349417 A1 | 12/2016 | Tearney et al. | |
| 2017/0020392 A1 | 1/2017 | Xu | |
| 2017/0024532 A1 | 1/2017 | Gopinath et al. | |
| 2017/0035281 A1 | 2/2017 | Takeuchi et al. | |
| 2017/0135584 A1 | 5/2017 | Tearney et al. | |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |
| 2018/0017778 A1 | 1/2018 | Ikuta et al. | |
| 2018/0271614 A1 | 9/2018 | Kunio | |
| 2019/0029623 A1 | 1/2019 | Kunio | |
| 2019/0029624 A1 | 1/2019 | Kunio | |
| 2020/0129740 A1* | 4/2020 | Kottenstette | G06V 10/25 |
| 2021/0137634 A1* | 5/2021 | Lang | A61B 5/113 |
| 2021/0142504 A1* | 5/2021 | Dascal | G06T 11/00 |

FOREIGN PATENT DOCUMENTS

| | | |
|---|---|---|
| WO | 2014/175853 A1 | 10/2014 |
| WO | 2015/045368 A1 | 4/2015 |
| WO | 2015/116939 A1 | 8/2015 |
| WO | 2015/116951 A2 | 8/2015 |
| WO | 2016/015052 A1 | 1/2016 |
| WO | 2016/144878 A1 | 9/2016 |
| WO | 2017/024145 A1 | 2/2017 |
| WO | 2017/117203 A1 | 7/2017 |
| WO | 2017/165511 A1 | 9/2017 |
| WO | 2019/023375 A2 | 1/2019 |
| WO | 2019/023382 A1 | 1/2019 |

OTHER PUBLICATIONS

Athanasiou, L.S., et al., "3D Reconstruction of Coronay Arteries using Frequency Domain Optical Coherence Tomography Images and Biplane Angiography", IEEE, Aug. 2012 (four pages).

Blondel, C., et al., "Reconstruction of Coronary Arteries From a Single Rotational X-Ray Projection Sequence", IEEE Transactions on Medical Imaging, vol. 25, No. 5, May 2006, pp. 653-663.

Bourantas, C. V., et al., "A new methodology for accurate 3-dimensional coronary artery reconstruction using routine intravascular ultrasound and angiographic data: implications for widespread assessment of endothelial shear stress in humans", Euro Intervention, vol. 9, Apr. 2013, pp. 582-593.

Bourantas, C. V., et al., "ANGIOCARE: An Automated System for Fast Three-Dimesional Coronary Reconstruction by Integrating Angiographic and Intracoronay Ultrasound Data", Catheterization and Cardiovascular Intervention, vol. 72, Apr. 2008, pp. 166-175.

Bourantas, C. V., et al., "Bioresorbable vascular scaffold treatment induces the formation of neointimal cap that seals the underlying plaque without compromising the luminal dimensions: a concept based on serial optical coherence tomography data", Euro Intervention, Oct. 2014, pp. 1-16.

Bourantas, C.V., et al., "A method for 3D reconstruction of coronary arteries using biplane angiography and Intravascular ultrasound images", Computerized Medical Imaging and Graphics, vol. 29, Nov. 2005, pp. 597-606.

(56) References Cited

OTHER PUBLICATIONS

Cardenes, R., et al., "3D Reconstruction of Coronary Arteries From Rotational X-Ray Angiography", IEEE, May 2012, pp. 618-621.

Coskun, A. U., et al., "Reproducibility of Coronary Lumen, Plaque, and Vessel Wall Reconstruction and of Endothelial Shear Stress Measurements In Vivo in Humans", Catheterization and Cardiovascular Interventions, vol. 60, Sep. 2003, pp. 67-78.

Ellwein, L.M., et al., Optical Coherence Tomography for Patient-specific 3D Artery Reconstruction and Evaluation of Wall Shear Stress in a Left Circumflex Coronary Artery, Cardiovascular Engineering and Technology, vol. 2, No. 3, Sep. 2011, pp. 212-227.

Giannoglou, G. D., et al., "In-vivo validation of spatially correct three-dimensional reconstruction of human coronary arteries by integrating intravascular ultrasound and biplane angiography", Diagnostic methods, vol. 17, No. 6, Sep. 2006, pp. 533-543.

Hebsgaard, L., et al., "Co-registration of optical coherence tomography and X-ray angiography in percutaneous coronary intervention. The Does Optical Coherence Tomography Optimize Revascularization (DOCTOR) fusion study" International Journal of Cardiology, vol. 182, Mar. 2015, pp. 272-278.

Hoffmann, K. R., et al., "Biplane X-ray angiograms, intravascular ultrasound, and 3D visualization of coronary vessels", International Journal of Cardiac Imaging, vol. 15, Dec. 1999, pp. 495-512.

Horsley, E., "Imaging for the Future . . . Intravascular Optical Coherence Tomography", Sep. 10, 2016; from https://www.slideshare.net/ErnestHorsley/coronary-optical-coherence-tomography-oct-angio-coregistration-acr-and-metal-stent-optimisation-mso-softwarefrom.

Kang, D., et al., "Three-Dimensional Blood Vessel Quantification via Centerline Deformation", IEEE Transations on Medical Imaging, vol. 28, No. 3, Mar. 2009, pp. 405-414.

Khaleel, H. H., et al., "A Review paper of 3D Surface Reconstruction of Coronary Arteries From Cardiovascular Angiography", 2012 International Conference on Advanced Computer Science Applications and Technologies (ACSAT), pp. 419-435, Nov. 2012, DOI: Doi 10.1109/Acsat.2012.13.

Klein, H. M., et al., "3D-Surface Reconstruction of Intravascular Ultrasound Images Using Personal Computer Hardware and a Motorized Catheter Control", Cardiovascular Interventional Radiology, vol. 15, Mar.-Apr. 1992, pp. 97-101.

Kraus, M.F., et al., "Motion correction in optical coherence tomography volumes on a per A-scan basis using orthogonal scan patterns", Bio. Med. Express, vol. 3, No. 6, Jun. 1, 2012, pp. 1182-1199.

Kumar, R.P., et al., "3D multiscale vessel enhancement based centerline extraction of blood vessels", Medical Imaging 2013: Image Processing, Proc. SPIE vol. 8669, Mar. 2013 (ten pages).

Laban, M., et al., "ANGUS: A New Approach to Three-Dimensional Reconstruction of Coronary Vessels by Combined Use of Angiography and Intravascular Ultrasound", Computers in Cardiology, IEEE, Oct. 1995, pp. 325-238.

Li, Y., et al., "Impact of Side Branch Modeling on Computation of Endothelial Shear Stress in Coronary Artery Disease: Coronary Tree Reconstruction by Fusion of 3D Angiography and OCT", Journal of the American College of Cardiology, vol. 66, Issue No. 2, Jul. 2015, pp. 125-135.

Maehara, et al., "Assessment and Quantification of Stent Results by Intracoronary Optical Coherence Tomography", Intervent. Cardiol. Clin., vol. 4, Issue 3, Jul. 2015, pp. 285-294.

Prati, et al., "Clinical Impact of OCT Findings During PCI: The CLI-OPCI II Study", JACC: Cardiovascular Imaging, vol. 8, No. 11, Nov. 2015, pp. 1297-1305.

Reiber, J., et al., "QCA, IVUS and OCT in interventional cardiology in 2011", Cardiovascular Diagnosis and Therapy, vol. 1, No. 1, Dec. 2011, pp. 57-70.

Rivest-Henault, D., et al., "Nonrigid 2D/3D Registration of Coronary Artery Models With Live Fluoroscopy for Guidance of Cardiac Interventions", IEEE Transations on Medical Imaging, vol. 31, No. 8, Aug. 2012, pp. 1557-1572.

Sarwal, A., et al., "Three dimensional reconstruction of coronary arteries from two views", Computer Methods and Programs in Biomedicine, vol. 65, Issue 1, Jan. 2001, pp. 25-43, ISSN: 0169-2607.

Shekhar, R., et al., "Fusion of Intravascular Ultrasound and Biplane Angiography for Three-Dimensional Reconstruction of Coronary Arteries", IEEE, Computers in Cardiology, Sep. 1996, pp. 5-8.

Slager, C. J., et al., "True 3-Dimensional Reconstruction of Coronary Arteries in Patients by Fusion of Angiography and IVUS (ANGUS) and its Quantitative Validation", vol. 102, No. 5, Aug. 2000, pp. 511-516.

St Jude Web Page, "OPTIS Stent Optimization Software", Last updated Feb. 10, 2017: https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f (three pages included).

Subramanian, K. R., et al., "Accurate 3D reconstruction of complex blood vessel geometries from intravascular ultrasound images: in vitro study", Journal of Medical Engineering & Technology, vol. 24, No. 4, Jul./Aug. 2000, pp. 131-140.

Timmins, L. H., et al., "Framework to Co-register Longitudinal Virtual Histology-Intravascular Ultrasound Data in the Circumferential Direction", IEEE Transactions on Medical Imaging, vol. 32, No. 11, Nov. 2013, pp. 1989-1996.

Tu, S., et al., "Fusion of 3D QCA and IVUS/OCT", International Journal of Cardiovascular Imaging, vol. 27, Issue 2, Feb. 2011, pp. 197-207.

Tu, S., et al., "Assessment of obstruction length and optimal viewing angle from biplane X-ray angiograms", Int. J. Cardiovasc. Imaging, vol. 26, No. 1, Jan. 2010, pp. 5-17.

Tu, S., et al., "In vivo comparison of arterial lumen dimensions assessed by co-registered three-dimensional (3D) quantitative coronary angiography, intravascular ultrasound and optical coherence tomography", Int. J. Cardiovasc. Imaging, vol. 28, No. 6, Aug. 2012, pp. 1315-1327.

Tu, S., et al., "In Vivo Flow Simulation at Coronary Bifurcation Reconstructed by Fusion of 3-Dimensional X-ray Angiography and Optical Coherence Tomography", Circ. Cardiovasc. Interv., vol. 6, No. 2, Apr. 2013, pp. e15-e17 (5 pages included).

Van Der Giessen, A., et al., "3D fusion of intravascular ultrasound and coronary computed tomography for in-vivo wall shear stress analysis: a feasibility study", Int. J. Cardiovasc. Imaging, vol. 26, No. 7, Oct. 2010, pp. 781-796.

Wahle, A., et al., "Fusion of Angiography and Intravascular Ultrasound in vivo: Establishing the Absolute 3-D Frame Orientation", IEEE Transactions on Biomedical Engineering, vol. 46, No. 10, Oct. 1999, pp. 1176-1180.

Wahle, A., et al., "Geometrically Correct 3-D Reconstruction of Intravascular Ultrasound Images by Fusion with Biplane Angiography—Methods and Validation", IEEE Transactions on Medical Imaging, vol. 18, No. 8, Aug. 1999, pp. 686-699.

Yang, J., et al., "Novel Approach for 3-D Reconstruction of Coronary Arteries from Two Uncalibrated Angiographic Images", IEEE Transactions on Image Processing, vol. 18, No. 7, Jul. 2009, pp. 1563-1572.

Zhang, W., et al., "3D Vessel Tree Reconstruction from Rotational C-arm Projections by Multi-view Stereo Reconstruction", APCMBE 2008: 7th Asian-Pacific Conference on Medical and Biological Engineering, IFMBE Proceedings, vol. 19, Jan. 2008, pp. 434-441, ISBN: 1680-0737.

Giovanni Jacopo Ughi, et al., "Clinical Characterization of Coronary Atherosclerosis With Dual-Modality OCT and Near-Infrared Autofluorescence Imaging", JACC: Cardiovascular Imaging, Nov. 2016 (In press), pp. 1-11.

Oubel, et al., "Analysis of Intracranial Aneurysm Wall Motion and its Effects on Hemodynamic Patterns", Proc. SPIE, Medical Imaging, vol. 6511, Mar. 2007 (eight pages included).

(56) References Cited

OTHER PUBLICATIONS

Dehkordi, et al., "Extraction of the Best Frames in Coronary Angiograms for Diagnosis and Analysis", J Med Signals, Sens. Jul.-Sep. 2016, 6(3): pp. 150-157 (14 pages included).

* cited by examiner

APPARATUSES, SYSTEMS, METHODS AND STORAGE MEDIUMS FOR PERFORMANCE OF CO-REGISTRATION

CROSS-REFERENCE TO RELATED APPLICATION(S)

This application relates, and claims priority, to U.S. Prov. Patent Application Ser. No. 62/798,885, filed Jan. 30, 2019, the disclosure of which is incorporated by reference herein in its entirety.

FIELD OF THE INVENTION

The present disclosure relates generally to the field of medical imaging and processing medical image data, and more particularly to apparatuses, systems, and methods and storage mediums for use therewith, that use a medical image frame to perform co-registration.

BACKGROUND OF THE INVENTION

Percutaneous coronary intervention (PCI) has been improved dramatically by innovative imaging modalities, such as coronary angiography and intravascular imaging. Coronary angiography provides longitudinal silhouettes of coronary arteries, while intravascular imaging modalities provide cross-sectional information of coronary arteries. Since intravascular imaging, such as intravascular ultrasound (IVUS) and optical coherence tomography (OCT), provides more precise lesion information, e.g., lumen size, plaque morphology, and implanted device, a system that enables physicians to connect (i.e., coregister) between two different imaging modalities was developed. One of the currently available methods requires generating a vessel centerline for coregistration from angiography data that is simultaneously acquired during IVUS/OCT pullback. The other one requires generating an imaging catheter path from angiography data that is acquired prior to IVUS/OCT pullback with user inputs.

More specifically, coronary angiography imaging and intravascular imaging are important imaging modalities for percutaneous coronary intervention (PCI). A coronary angiography provides longitudinal silhouettes of coronary arteries as aforementioned. The longitudinal silhouettes of the coronary artery are displayed on a monitor to help an interventional cardiologist guide a catheter insertion to a targeted region. Using coronary angiography during a PCI procedure may be preferred because it is easier to guide the catheter to a lesion than other types of imaging modalities.

Another imaging modality used in PCI is intravascular imaging which provides cross-sectional information of coronary arteries as aforementioned. Intravascular imaging may include intravascular ultrasound (IVUS) and optical coherence tomography (OCT) that provides more precise lesion information, as aforementioned, than a coronary angiography image. However, relying only on an intravascular imaging modality such as IVUS or OCT in a PCI procedure is difficult when guiding a catheter to a targeted region such a lesion to gain information about a lumen size, plaque morphology or implanted devices by way of example.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

A system that enables physicians to connect between two different imaging modalities including for example both coronary angiography and intravascular imaging during PCI involves co-registration. Co-registration (also referred to herein as "coregistration") refers to the spatial alignment of a series of images. For example, co-registration may refer to the alignment of functional (intravascular imaging) and anatomical images (coronary angiography) of a patient who undergoes PCI to map functional information into anatomical space. One benefit associated with co-registering angiography imaging with intravascular imaging includes determining where along the longitudinal silhouette of the coronary artery in an angiography image frame the intravascular image was acquired. However, current methods cannot provide the co-registration feature unless the angiography image is acquired to satisfy its requirement.

Accordingly, it would be desirable to provide at least one imaging (e.g., IVUS, OCT, etc.) technique (and/or at least one feature or option), storage medium and/or apparatus or system for use in at least one optical device, assembly or system to efficiently achieve co-registration result(s), especially in a way that reduces or minimizes cost of manufacture and maintenance.

SUMMARY OF THE INVENTION

Accordingly, it is a broad object of the present disclosure to provide imaging (e.g., IVUS, OCT (for example, but not limited to, using an interference optical system, such as an interferometer (e.g., SD-OCT, SS-OCT, etc.)), etc.) apparatuses and systems that operate to select (e.g., automatically) an appropriate method and perform co-registration based on at least one condition (or a plurality of conditions) of an available angiography image, and methods and storage mediums for use with same. One or more embodiments may achieve a co-registration result under any imaging circumstances. For example, at least one embodiment may have multiple methods of co-registration and may pick the most appropriate algorithm/method of co-registration based on the imaging that is available for co-registration. One or more embodiments may automatically select a co-registration method based on at least one angiography data condition, and may achieve functionality where a user may not have to manually select a co-registration method and/or where a user may not have to consider how to acquire angiography data. One or more embodiments, may achieve functionality where a user may not have to manually select a co-registration method and/or where a user may not have to consider how to acquire imaging data for any imaging modality.

It is also a broad object of the present disclosure to provide imaging apparatuses, systems, methods and storage mediums to the field of minimally invasive medical imaging devices, including, but not limited to, intravascular ultrasound (IVUS) and optical coherence tomography (OCT). One or more embodiments of the present disclosure enable providing one or more co-registration features for any cases or procedures. One or more embodiments may prepare multiple algorithms for co-registration with different requirements of angiography image acquisition and may automatically select the algorithm(s) based on the angiography image input to provide co-registration feature(s) for any input type of angiography image. More generally stated, by using the configuration(s) and function(s)/option(s)/technique(s) discussed herein, co-registration feature(s) may be provided for any type of angiography image provided or input.

In accordance with one or more embodiments of the present disclosure, imaging (e.g., OCT, IVUS, etc.) apparatuses and systems, and methods and storage mediums may operate to characterize tissue type in addition to providing a morphological image to help an operator's diagnostic decision based on quantitative tissue information. In accordance with one or more embodiments of the present disclosure, imaging (e.g., OCT, IVUS, etc.) apparatuses and systems, and methods and storage mediums may operate to characterize biological objects other than tissue. For example, the characterization may be of a biological fluid such as blood or mucus (e.g., using OCT, such as, but not limited to, multimodality optical coherence tomography (MM-OCT)).

One embodiment of the present disclosure is directed to at least one processor selecting an appropriate option for co-registration with a given angiography image input.

One embodiment of the present disclosure is directed to a method for displaying an anatomical image of a coronary artery on a graphical user interface. The method may initiate with acquiring an anatomical image or multiple anatomical images of a coronary artery and acquiring a plurality of intravascular image frames of the coronary artery associated with the anatomical image at a plurality of acquisition locations.

Another embodiment of the present disclosure is directed to a method for displaying one or more options for initiating a process for co-registration (also referred to herein as a co-registration process) on a graphical user interface ("GUI" or "UI"). One or more embodiments may display queries on a UI for a user to select whether to obtain another angiography image to perform co-registration, or indications/messages on a UI, such as, but not limited to, to let the user know that the apparatus/system cannot perform co-registration at that time, to let the user know that co-registration is under process and to indicate what kind of angiography data is used in the co-registration, etc.

In one or more embodiments of the present disclosure, it is possible to, in imaging (e.g., IVUS, OCT, etc.), reduce the size of the optical apparatus and/or system and acquire black and white and/or color images. That said, in one or more embodiments, size reduction may not be an issue in a case where it is possible to specify a location of the pullback (e.g., IVUS pullback, OCT pullback, etc.) in an image, such as, but not limited to, an angiography image.

In one or more embodiments, a target area (e.g., a blood vessel) may flushed with a flushing media or agent and/or a contrast agent (in one or more embodiments, the flushing media or agent may include or encompass a contrast agent), and then pullback of the imaging probe or catheter is performed to acquire the one or more images.

According to other aspects of the present disclosure, one or more additional apparatuses, one or more systems, one or more methods, and one or more storage mediums using co-registration and/or features/functions/techniques to select an appropriate co-registration method based on available imaging condition(s), such as, but not limited to, angiography image condition(s), are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE EMBODIMENTS

Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope; arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus.

One or more devices, optical systems, methods, and storage mediums for obtaining a direct image (e.g., black and white, color, etc.) of a subject, such as tissue, using an imaging function, feature, technique or method; a coregistration function, feature, technique, or method; and/or selecting an appropriate co-registration method, and/or for diagnosing, irrigating, suctioning, dilating (e.g., balloon), culturing, tissue sampling, performing a biopsy, implanting a drug and/or performing any other type of diagnosis and/or treatment using an imaging feature, function or technique are disclosed herein. In accordance with at least one aspect of the present disclosure, one or more devices, optical systems, methods, and storage mediums discussed herein use an imaging function, feature, technique or method; a coregistration function, feature, technique or method; and/or selecting an appropriate co-registration method.

Figure 1:
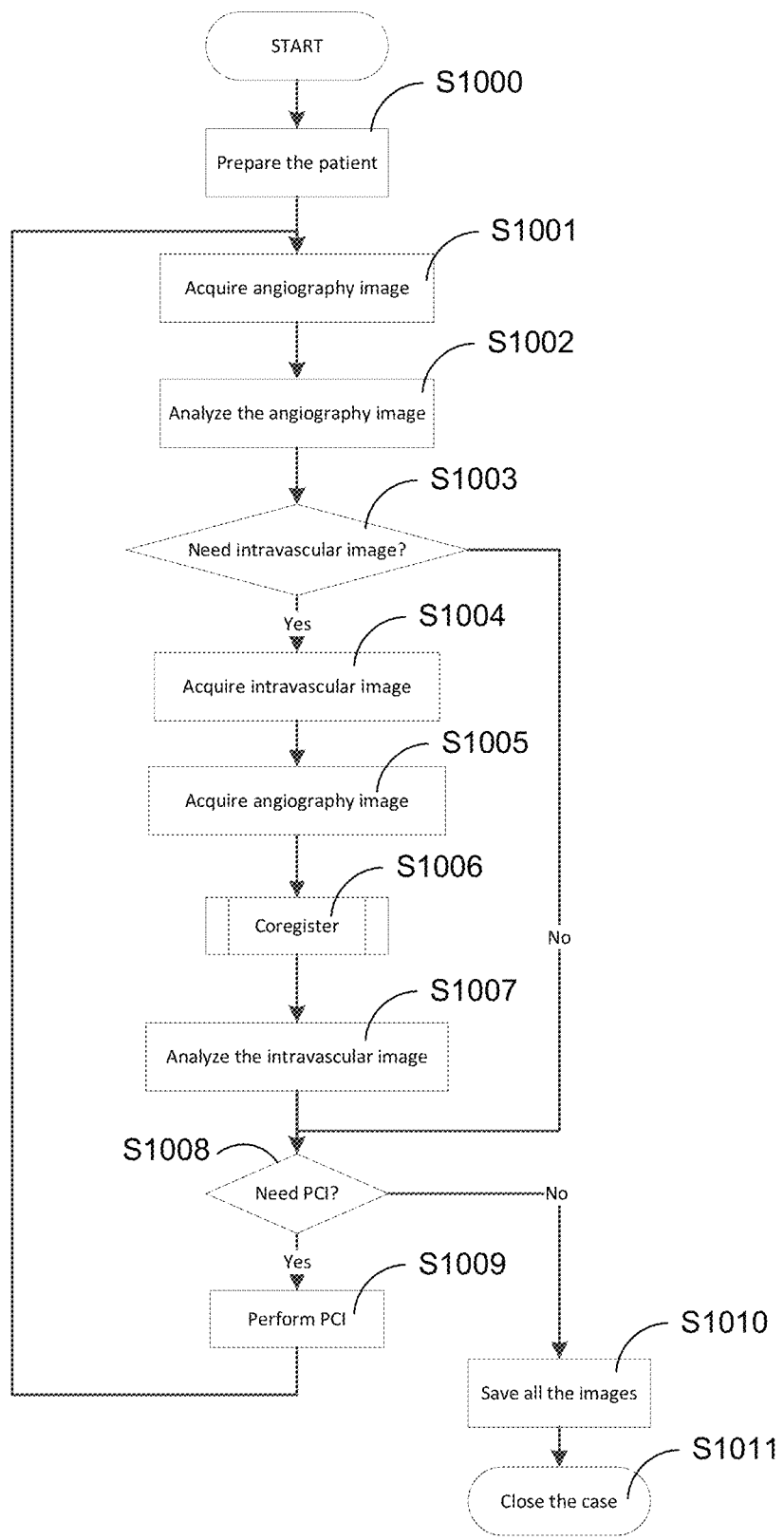
FIG. 1 shows at least one embodiment of an overall workflow in a catheterization laboratory in accordance with one or more aspects of the present disclosure.

In one or more embodiments, multiple imaging modalities may be used to plan a procedure and confirm procedural success of percutaneous coronary intervention (PCI) in a catheterization laboratory at a hospital. FIG. 1 shows at least one embodiment example of an overall workflow in a catheterization laboratory. In one or more embodiments, such a method may include the following steps: (i) preparing a patient (such as the patient 28 discussed below) (see e.g., step S1000 in FIG. 1); (ii) acquiring at least one angiography image (see e.g., step S1001 in FIG. 1); (iii) analyzing the angiography image (see e.g., step S1002 in FIG. 1); (iv) determining whether an intravascular image is needed (see e.g., step S1003 in FIG. 1), and, if "No", proceed to step S1008 discussed below, or, if "Yes", proceed to steps S1004-S1008; (v) if an intravascular image is needed in step S1003, then acquiring the intravascular image (see e.g., step S1004 in FIG. 1); (vi) acquiring the angiography image (see e.g., step S1005 in FIG. 1); (vii) performing coregistration (see e.g., step S1006 in FIG. 1); (viii) analyzing the intravascular image (see e.g., step S1007 in FIG. 1); (ix) determining whether PCI is needed (see e.g., step S1008 in FIG. 1), and, if "Yes", (x) perform the PCI (see e.g., step S1009 in FIG. 1) and then return to step S1001, or, if "No", (xii) saving all of the images (see e.g., step S1010 in FIG. 1) and then closing the case (see e.g., step S1011 in FIG. 1). Angiography shows a global view of coronary artery trees of a patient. Intravascular imaging modalities, such as intravascular ultrasound (IVUS), optical coherence tomography (OCT), and multimodality OCT (MM-OCT), may provide information in vessel walls by capturing cross-sectional views of the targeted coronary artery. In one or more embodiments, a method to select an appropriate method to coregister one or more intravascular images with one or more angiography images based on how at least one angiography image is acquired is described. Coregistration between an intravascular image and an angiography image may help physicians/practitioners connect information from different imaging modalities and understand one or more condition(s) of the patient.

Figure 2:
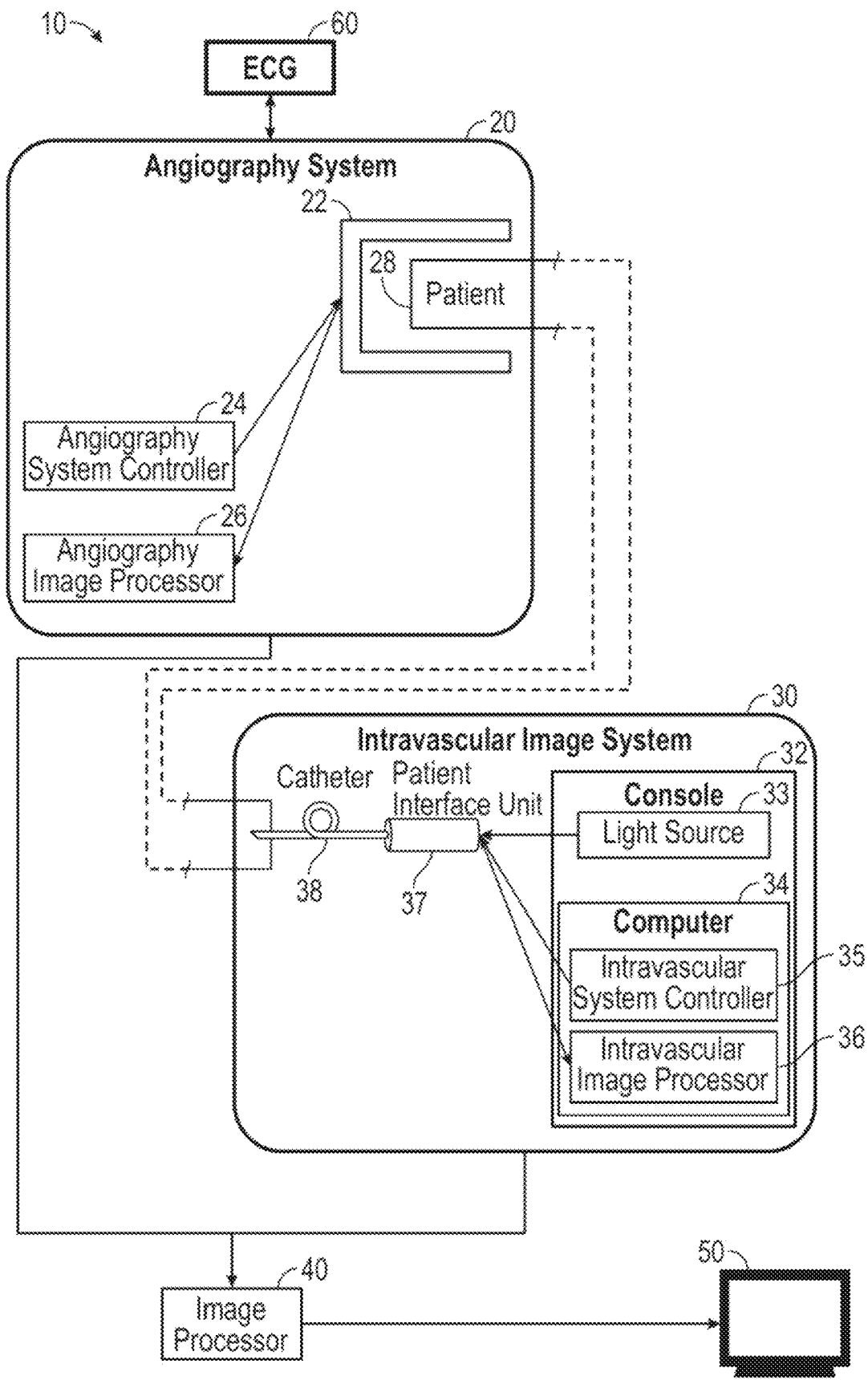
FIG. 2 shows a structure of at least one embodiment of a multimodality optical coherence tomography (MM-OCT) apparatus or system in accordance with one or more aspects of the present disclosure.

FIG. 2 is a schematic diagram of at least two of the imaging modalities (e.g., angiography, intravascular imaging, etc.) and the connection therebetween that are referred in the following descriptions as at least one embodiment example of an imaging system 10. The imaging system 10 embodiment may include an angiography system 20, an intravascular imaging system 30, at least one processor (e.g., one or more processors (see e.g., computer or processor 1200, computer or processor 1200', etc.), an image processor 40, etc.), a display/monitor 50 (see also, display or screen 1209 shown in at least FIGS. 21-22 discussed below), and a device to detect cardiac motion (e.g., electrocardiography (ECG) device 60) are used in this method embodiment example. An angiography system 20 may include an X-ray imaging device (e.g., a C-arm 22 as shown in FIG. 2), a system controller 24 (e.g., connected to the X-ray imaging device), and at least one processor (e.g., an image processor 26) that may operate to acquire angiography image frames of an object, subject, patient 28, etc. An intravascular imaging system 30 may include a console 32, a catheter 38, and a patient interface unit 37 that connects, and extends between, the catheter 38 and the console 32 (e.g., for acquiring intravascular image frames). The catheter 38 may be inserted into the patient 28, object, sample, etc. (e.g., into a blood vessel of a patient). The catheter 38 may function as a light irradiator and a data collection probe that is disposed in the lumen of a particular blood vessel, such as for example, a coronary artery. The catheter 38 may include a probe tip, one or more radiopaque markers, an optical fiber, and a torque wire. The probe tip may include one or more data collection systems. The catheter 38 may be threaded in a patient's artery to obtain images of the coronary artery. A patient interface unit 37 may have a motor inside to enable pullback of imaging optics during acquisition of intravascular image frames. The imaging pullback procedure may obtain images of the predetermined area, such as the blood vessel, of the object, target, patient, etc. The imaging pullback path may represent the co-registration path which may be a region of interest or a targeted region of the predetermined area (e.g., the blood vessel). A console 32 may include a computer 34 and one or more light source(s) 33. A processor of a computer 34 may control the motor in the patient interface unit 37, may perform all the steps for image processing, and may control the information to be displayed on the monitor 50 (or 1209 as discussed below). The computer 34 may include an intravascular system controller 35 and an intravascular image processor 36. The intravascular image processor 36 may control the motor in the PIU 37. The intravascular image processor 36 may also perform various steps for image processing and control the information to be displayed. The at least one processor or an image processor 40 (see also, computer or processor 1200, computer or processor 1200', etc.) may be an external processor as shown diagrammatically in FIG. 2, and, additionally or alternatively, the at least one processor or the image processor 40 may be a processor in the angiography system or in the intravascular imaging system. In one or more embodiments, a computer or processor (such as, but not limited to, the image processor 40, the computer or processor 1200, the computer or processor 1200', any other processor discussed herein, etc.) may perform one or more of the features of any other processor discussed herein (e.g., the angiography image processor 26, the intravascular image processor 36, the angiography system controller 24, the intravascular system controller 35, a combination thereof, etc.)

Figure 3:
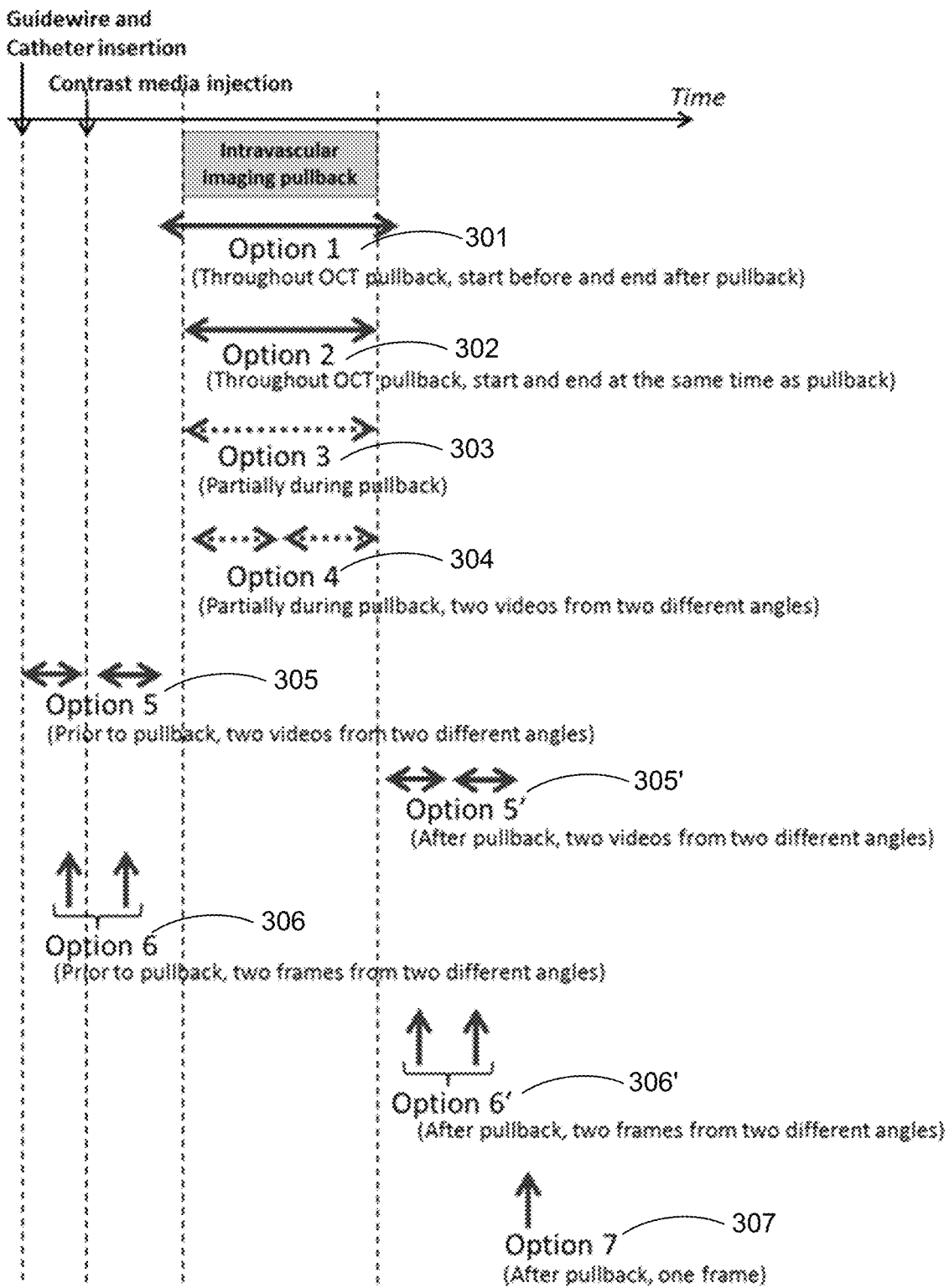
FIG. 3 shows embodiment examples of options when an angiography image may be acquired relative to the intravascular imaging pullback for co-registration in accordance with one or more aspects of the present disclosure.
Figure 4:
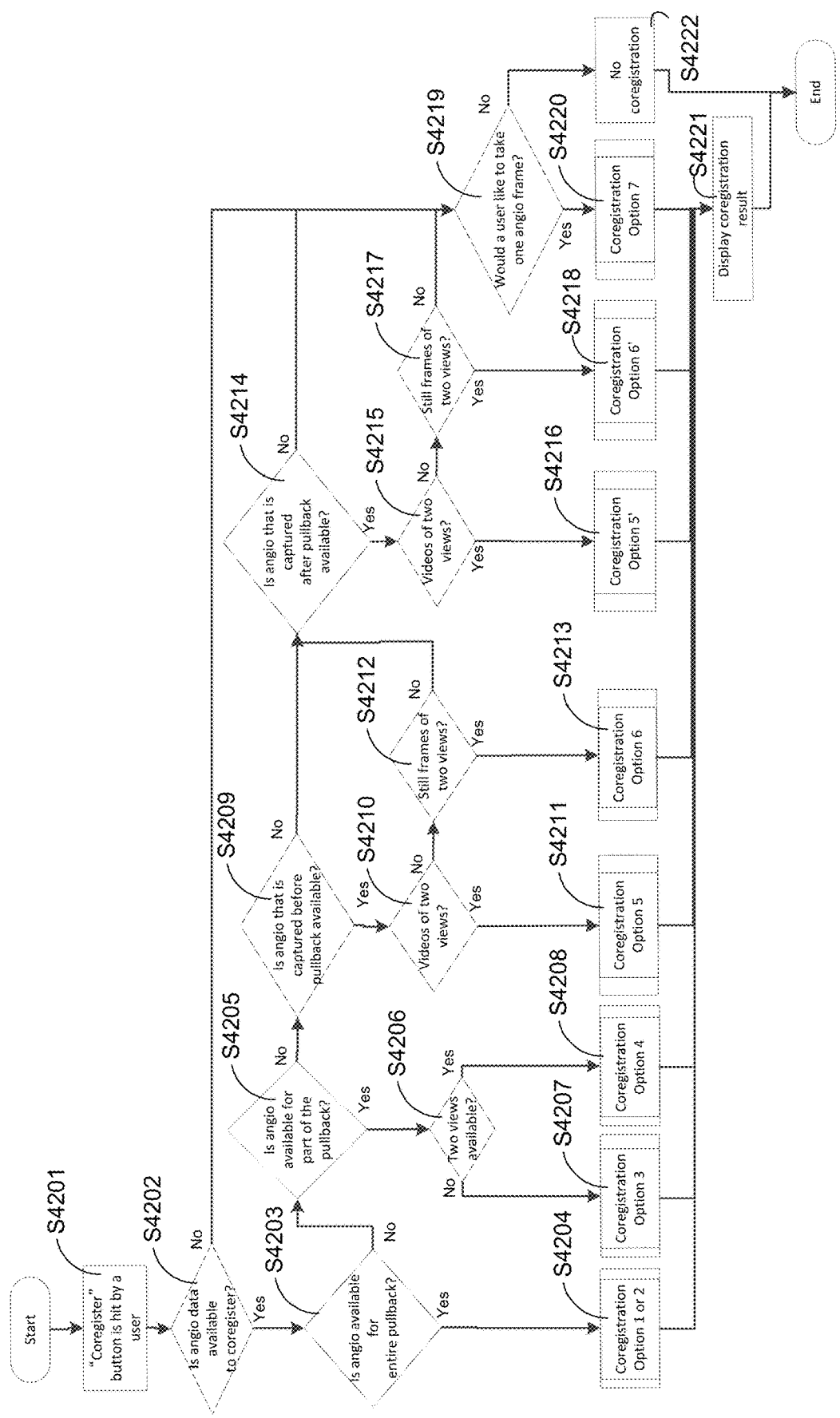
FIG. 4 shows a flowchart of at least one embodiment of how one or more processors select an appropriate option for coregistration with a predetermined or given angiography image input in accordance with one or more aspects of the present disclosure.
Figure 5:
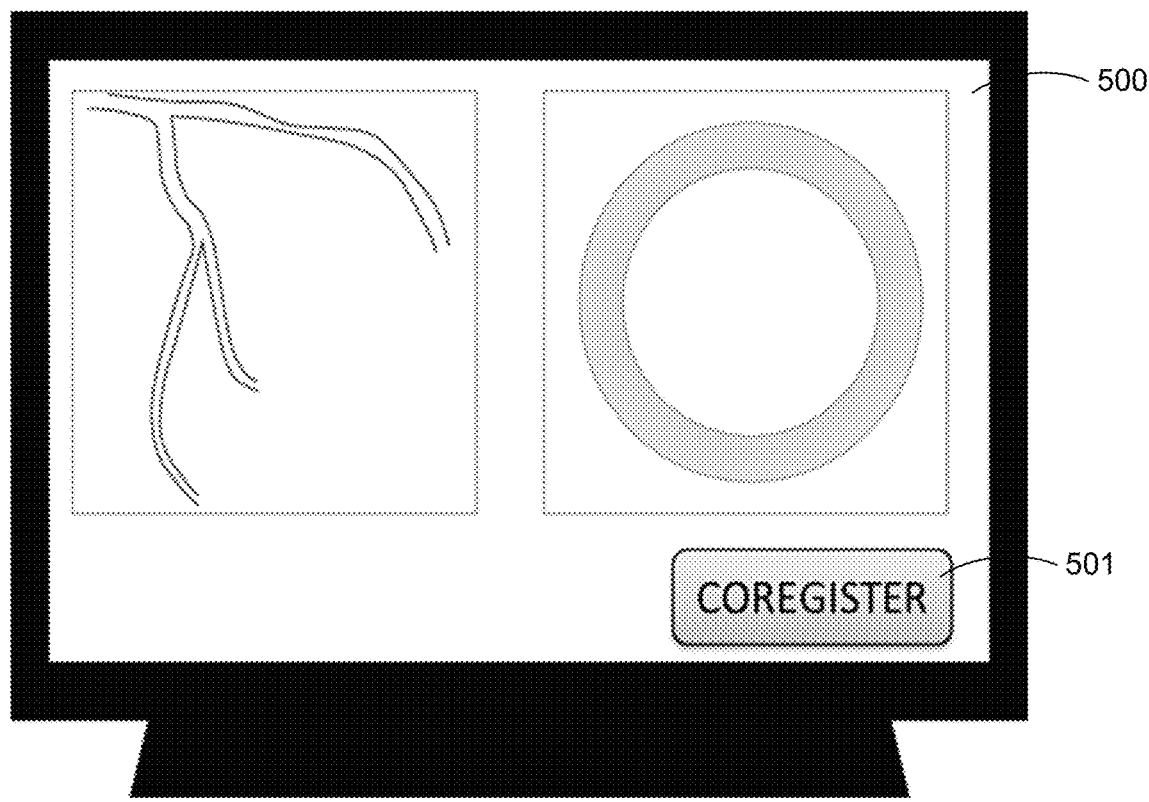
FIG. 5 shows an embodiment example of at least one UI for a user to initiate a coregistration process or processes in accordance with one or more aspects of the present disclosure.
Figure 6:
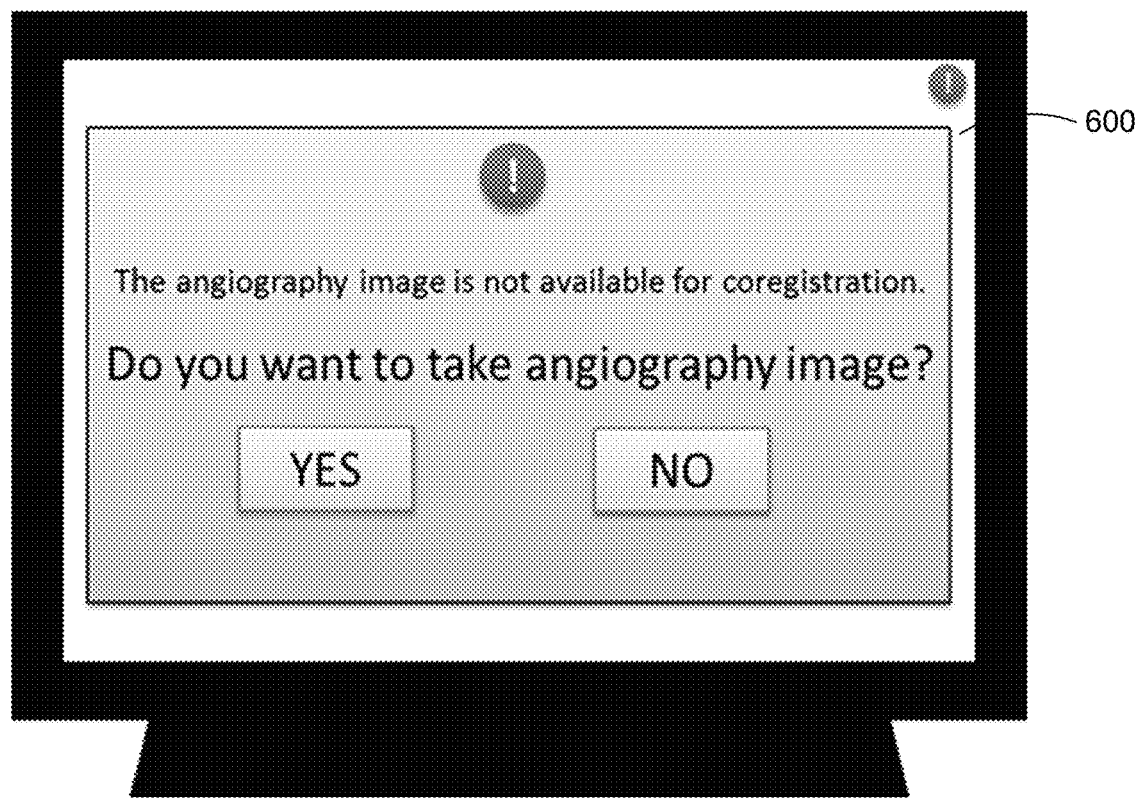
FIG. 6 is an embodiment example of at least one UI to ask a user to obtain another angiography image to perform coregistration in accordance with one or more aspects of the present disclosure.
Figure 7:
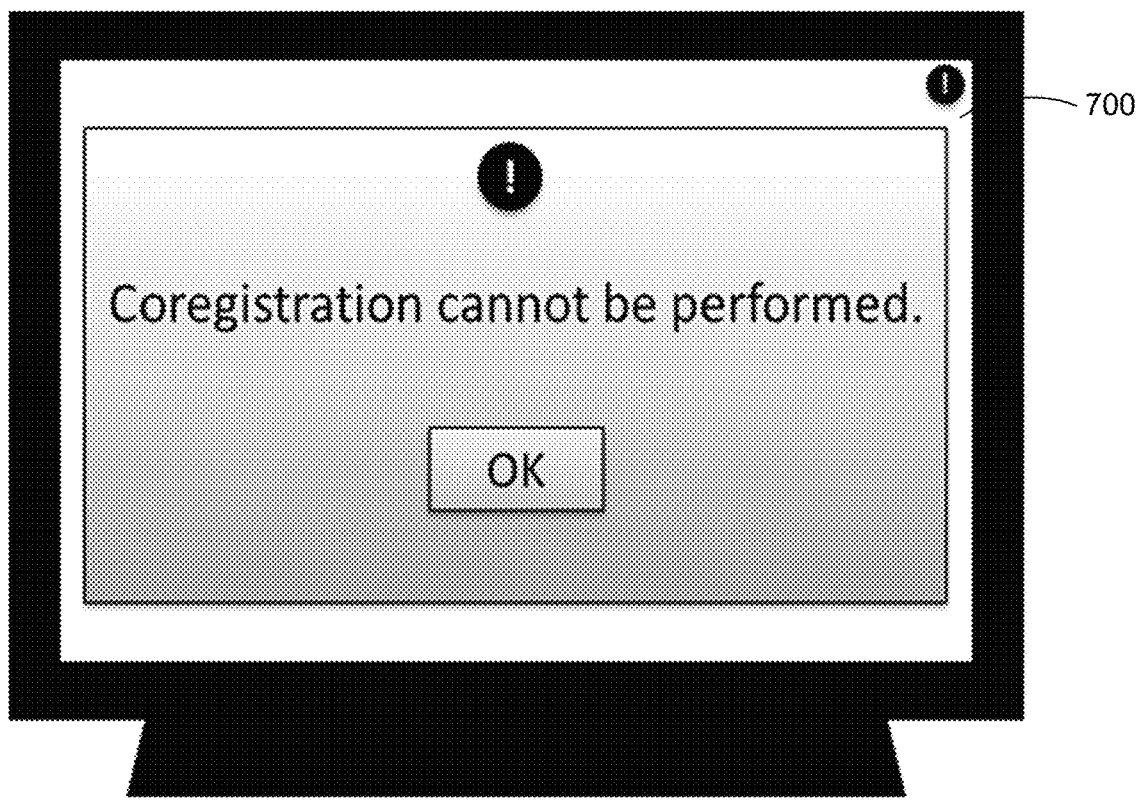
FIG. 7 is an embodiment example of at least one UI to let a user know that the system may not be able to perform coregistration at a particular time or times in accordance with one or more aspects of the present disclosure.
Figure 8:
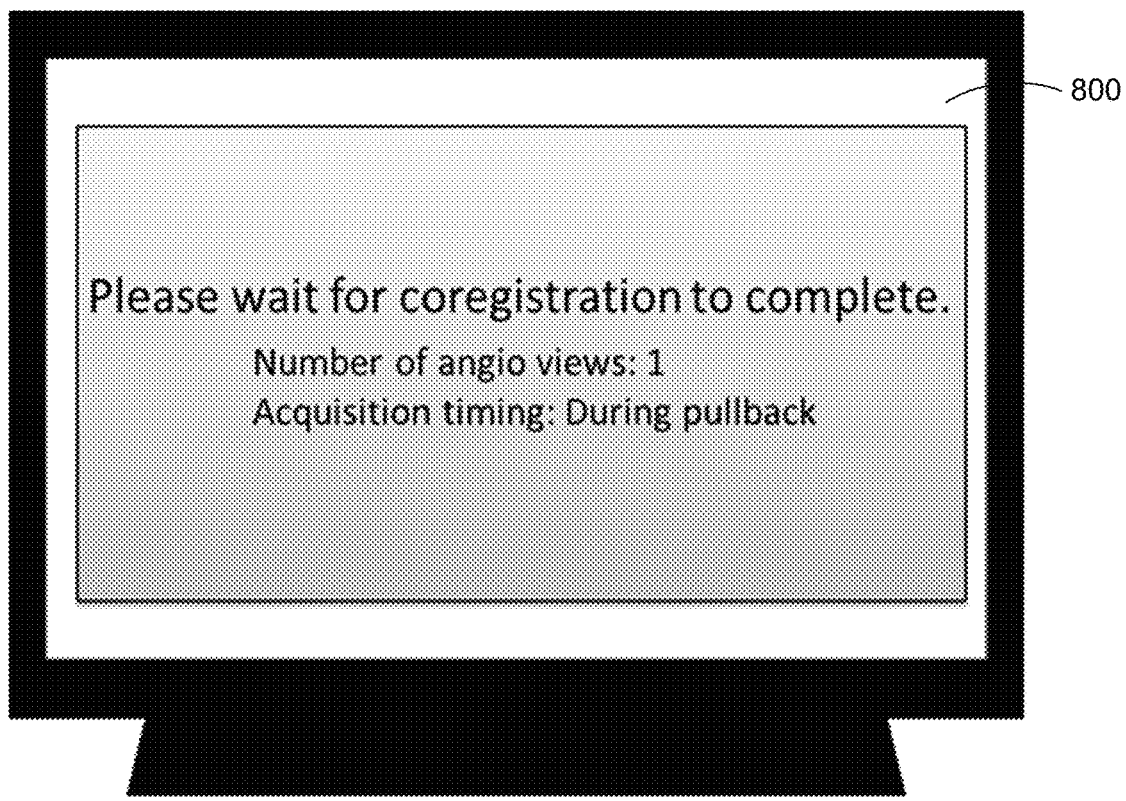
FIG. 8 is an embodiment example of at least one UI to let a user know that coregistration is under process or has started and to indicate what kind of angiography data is used in the coregistration in accordance with one or more aspects of the present disclosure.

Details of one or more embodiments are shown in FIGS. 3-8 of the present disclosure. FIG. 3 describes one or more options (in at least one embodiment, FIG. 3 shows all options when an angiography image may be acquired relative to the intravascular imaging pullback for coregistration) of the timings when the angiography image may be acquired relative to the timing of an intravascular imaging pullback. FIG. 4 shows how one or more image processors (and/or other types of processors or computers, such as, but not limited to, the computer or processor 1200, the computer or processor 1200', any other computer or processor discussed herein, etc.) select an appropriate coregistration method or option once a user initiates a coregistration process (e.g., FIG. 4 shows a flowchart of how an image processor may select an appropriate option for coregistration (see e.g., step S1006 in FIG. 1) with a given angiography image input). An example user interface (UI) 500 for at least one embodiment example of an initiation (e.g., allowing a user to initiate a coregistration process) is shown in FIG. 5. In this example UI 500, once the intravascular imaging pullback is finished, the angiography image, if available, and the intravascular image may be displayed with a button 501 that says "coregister." Once a user hits the button 501 with a controller (e.g., a mouth or a bedside controller), the one or more image processors start selecting an appropriate coregistration algorithm as a first step of a coregistration process (see e.g., step S1006 in FIG. 1; see e.g., step S4001 as shown in FIG. 4). If (or in a case where) the angiography image is captured throughout the intravascular imaging pullback (see e.g., "Yes" in step S4203 in FIG. 4), Option 1 301 or Option 2 302 (as shown in FIG. 3) may be selected in one or more embodiments (see e.g., step S4204 in FIG. 4). The difference between Options 1 and 2 301, 302 is that the starting time and ending time of the angiography image is before and after the intravascular imaging pullback (Option 1 301) or simultaneous to the intravascular imaging pullback (Option 2 302) as best seen in FIG. 3. If (or in a case where) the angiography image is not captured throughout the intravascular imaging pullback (see e.g., "No" in step S4203 in FIG. 4), but is captured during some part of the pullback (see e.g., "Yes" in step S4205) in FIG. 4, the image processor (or any other processor) may select Option 3 303 or Option 4 304 (as shown in FIG. 3). Option 3 303 may be selected (see e.g., step S4207 in FIG. 4) when the angiography image is captured from only one angle (see e.g., "No" in a determination as to whether at least two views are available as shown in step S4206 in FIG. 4), while Option 4 may be selected (see e.g., step S4208 in FIG. 4) when the angiography image is captured from two or more angles (see e.g., "Yes" in the determination as to whether at least two views are available as shown in step S4206 in FIG. 4). If (or in a case where) the angiography image is not captured during the intravascular imaging pullback (see e.g., "No" in step S4205 in FIG. 4), but is captured before the pullback (see e.g., "Yes" in step S4209 in FIG. 4) from two or more angles (see e.g., "Yes" in step S4210 in FIG. 4), Option 5 305 may be selected (see e.g., step S4211 in FIG. 4) if multiple frames are contained in each angiography image (e.g., there may be two videos from two different angles), and Option 6 306 may be selected (see e.g., step S4213 in FIG. 4) if only one frame is contained in each angiography image (see e.g., "No" in step S4210 in FIG. 4 and "Yes" to step S4212 in FIG. 4 where there may only be video (or no video) and frames of two views). If (or in a case where) the angiography image is captured from two or more angles after the intravascular imaging pullback (see e.g., "No" in step S4209 in FIG. 4 or "No" in step S4212 in FIG. 4), Option 5' 305' (multiple frames in each angiography image) (see e.g., "Yes" in step S4214 and "Yes" in step S4215 in FIG. 4) or Option 6' 306' (one frame in each angiography image) (see e.g., "Yes" in step S4214, "No" in step S4215, and "Yes" in step S4217 in FIG. 4) may be selected (see e.g., step S4216 in FIG. 4 for Option 5' 305' and see e.g., step S4218 in FIG. 4 for Option 6' 306'). If (or in a case where), for any reasons, the angiography image is not delivered to the one or more image processors (or any other type of processor(s)), the intravascular imaging system may show another UI to ask a user whether the user would like to capture a new (or another) angiography image (see e.g., embodiment example of a UI 600 shown in FIG. 6) (see e.g., "No" in step S4202, "No" in step S4214, or "No" in step S4217 in FIG. 4). If (in a case where) a user selects to acquire another angiography image (see e.g., "Yes" in step S4219 in FIG. 4), the intravascular imaging system may let a user know when to start acquisition of angiography image using other UIs. After the new angiography image is acquired and delivered to the one or more image processors (or any other type of processor(s)), the one or more image processors (or other type of processor(s)) may select Option 7 307 (see e.g., step S422*o* in FIG. 4) and continue the coregistration process (e.g., the coregistration result may be displayed as shown in step S4221 in FIG. 4). Additionally or alternatively, Option 7 307 may be available in a case where other angiography imaging data and/or any other imaging (e.g., CT angiography) prior to the pullback (e.g., intravascular pullback) is available and a user would like to use the other imaging method or technique (and/or function or feature) instead of capturing angiography data as discussed further below. If (in a case where) a user chooses not to take a new angiography image (see e.g., "No" in step S4219 in FIG. 4), the intravascular imaging system may show an alert to notify a user that a coregistration feature may not be available (see e.g., step S4222 in FIG. 4; see also e.g., an embodiment example of a UI 700 showing that coregistration cannot be performed by a system at that time as shown in FIG. 7).

Once the appropriate co-registration algorithm/method or option is selected by the one or more image processors (and/or other type(s) of processor(s)), the processes for coregistration preferably start. Some algorithms may require user input, in which case, a series of UIs may navigate a user or request input from the user. While the one or more image processors (and/or other type(s) of processor(s)) run the coregistration processes, a user may be notified that coregistration is being performed (e.g., with a prompt to wait for coregistration to complete) and may be notified of the information of the angiography image (or any other type of angiography data) that is used in the coregistration processes (e.g., number of angio views, acquisition timing, etc. as shown in the example UI 800 of FIG. 8).

The coregistration (e.g., step S1006 in FIG. 1; one or more of the Options 1 through 7 in FIG. 3; one or more of the steps S4201 through S4222 in FIG. 4; and/or any other coregistration step or method discussed herein) may be performed with any available methods. One or more embodiments of example methods are described below.

Embodiment examples and details relating to Options 1 301 and 2 302 (shown in FIG. 3) are shown in the embodiments of FIGS. 9-12 of the present disclosure.

Since the distance between the radiopaque marker and the location on the catheter (see e.g., the catheter 38) where the intravascular image is captured is fixed in one or more embodiments, the actual acquisition location may be calculated based on this distance once the radiopaque marker location is defined in each angiography image frame. In one example way, since the radiopaque marker appears as a dark point in the angiography image due to its radiopacity, the dark point may be searched in each angiography image frame and tracked throughout the angiography image.

After the image acquisition of both angiography and intravascular images, both images may be sent or imported to at least one imaging processor. After that, a radiopaque marker may be detected in each angiography image frame, and a coregistration path may be generated based on the detected marker locations. Then, a location where each intravascular image is acquired in the global view of coronary artery tree may be searched and may be displayed on an angiography image to the display/monitor along with an intravascular image. Since the frame rate of the intravascular image may be higher than that of the angiography image in one or more embodiments, there are multiple intravascular frames of which acquisition location may not be determined directly from the angiography image using the detected marker locations. Therefore, generation of a coregistration path may be useful to determine the acquisition locations for the intravascular image that does not have the corresponding angiography image. There are two potentials as a coregistration path in one or more embodiments: a vessel centerline and an imaging catheter path. In this method, an imaging catheter may be selected to achieve a more accurate coregistration result—the imaging catheter path is the path that the intravascular image is actually acquired perpendicularly to, while the vessel centerline is a line that represents the vessel's longitudinal direction.

Figure 9:
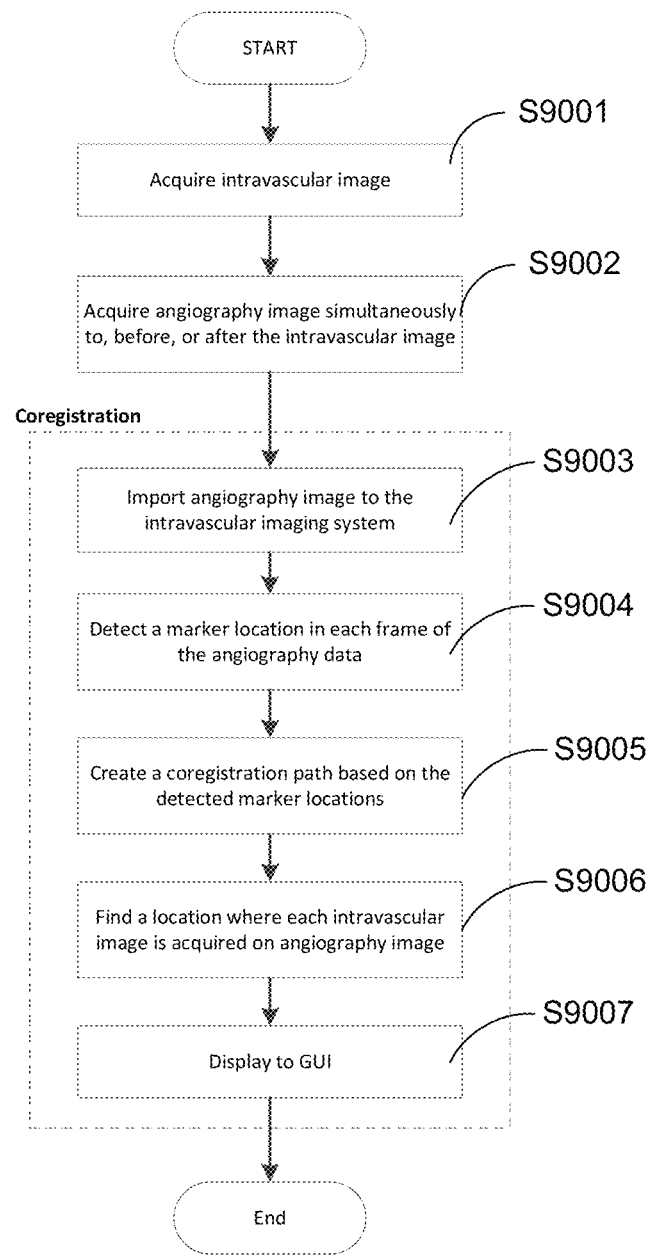
FIG. 9 shows at least one embodiment of an overall workflow of coregistration in accordance with one or more aspects of the present disclosure.
Figure 10A:
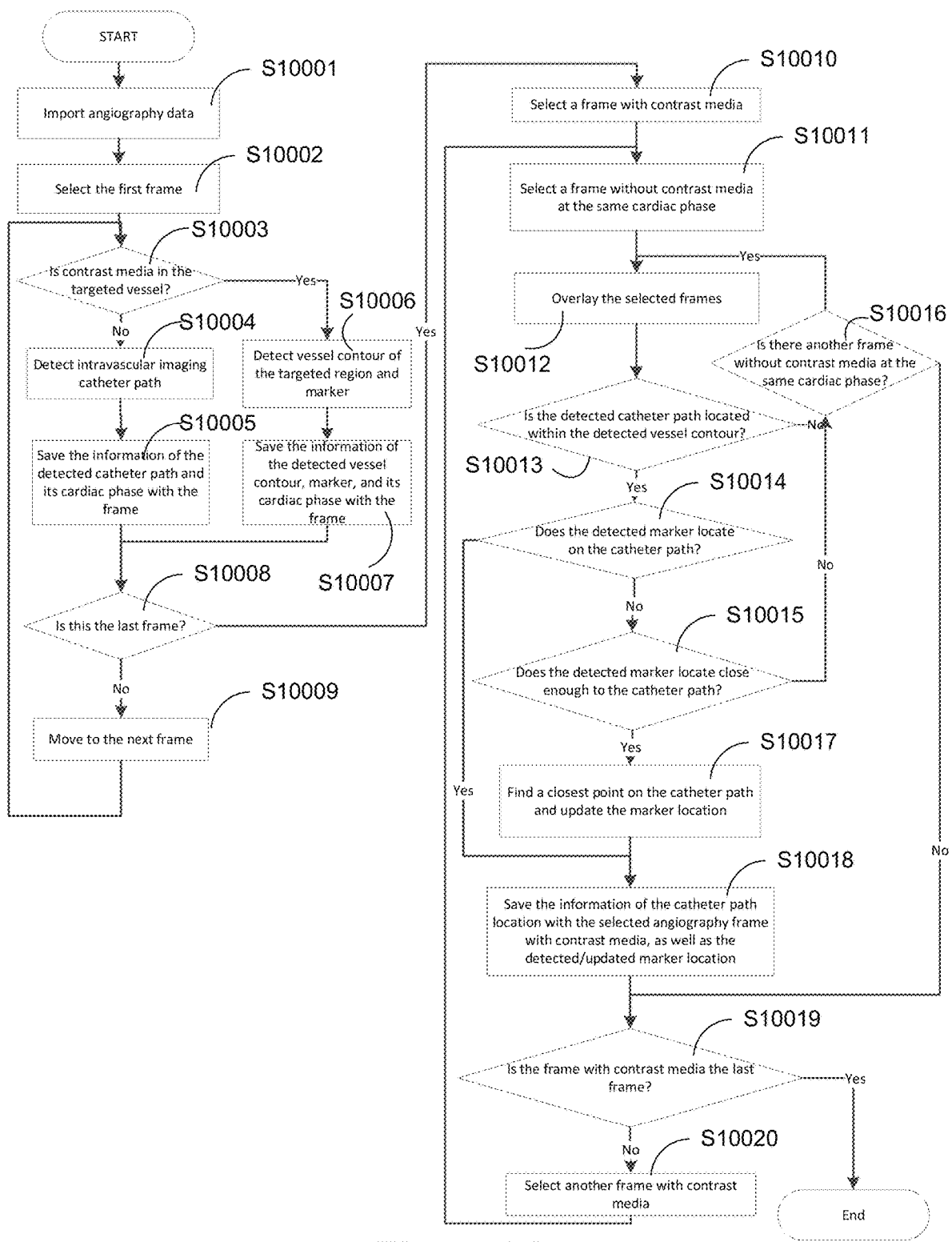
FIGS. 10A-10D describe one or more detailed steps of coregistration for at least one option in accordance with one or more aspects of the present disclosure.
Figure 10B:
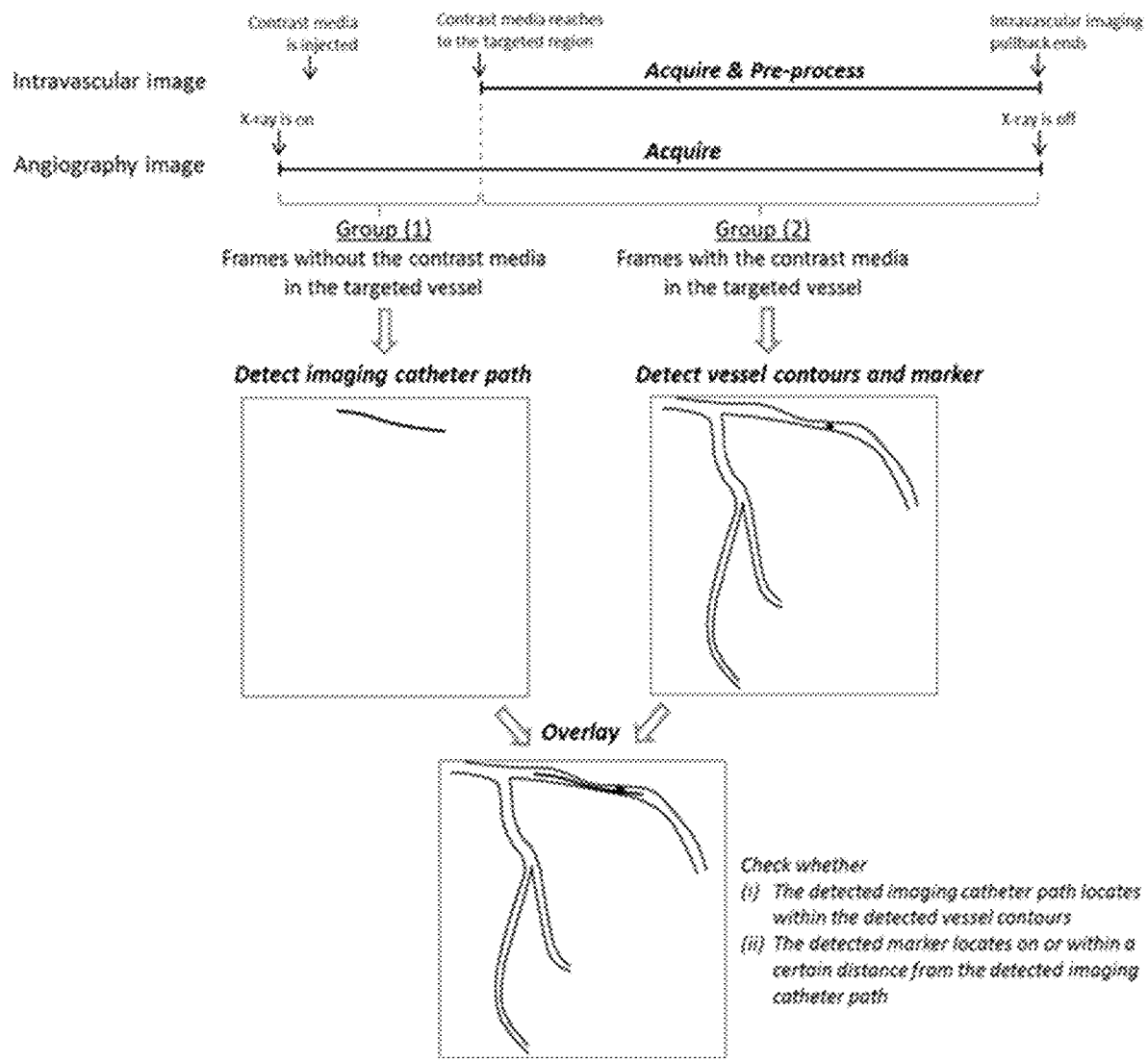
Figure 10C:
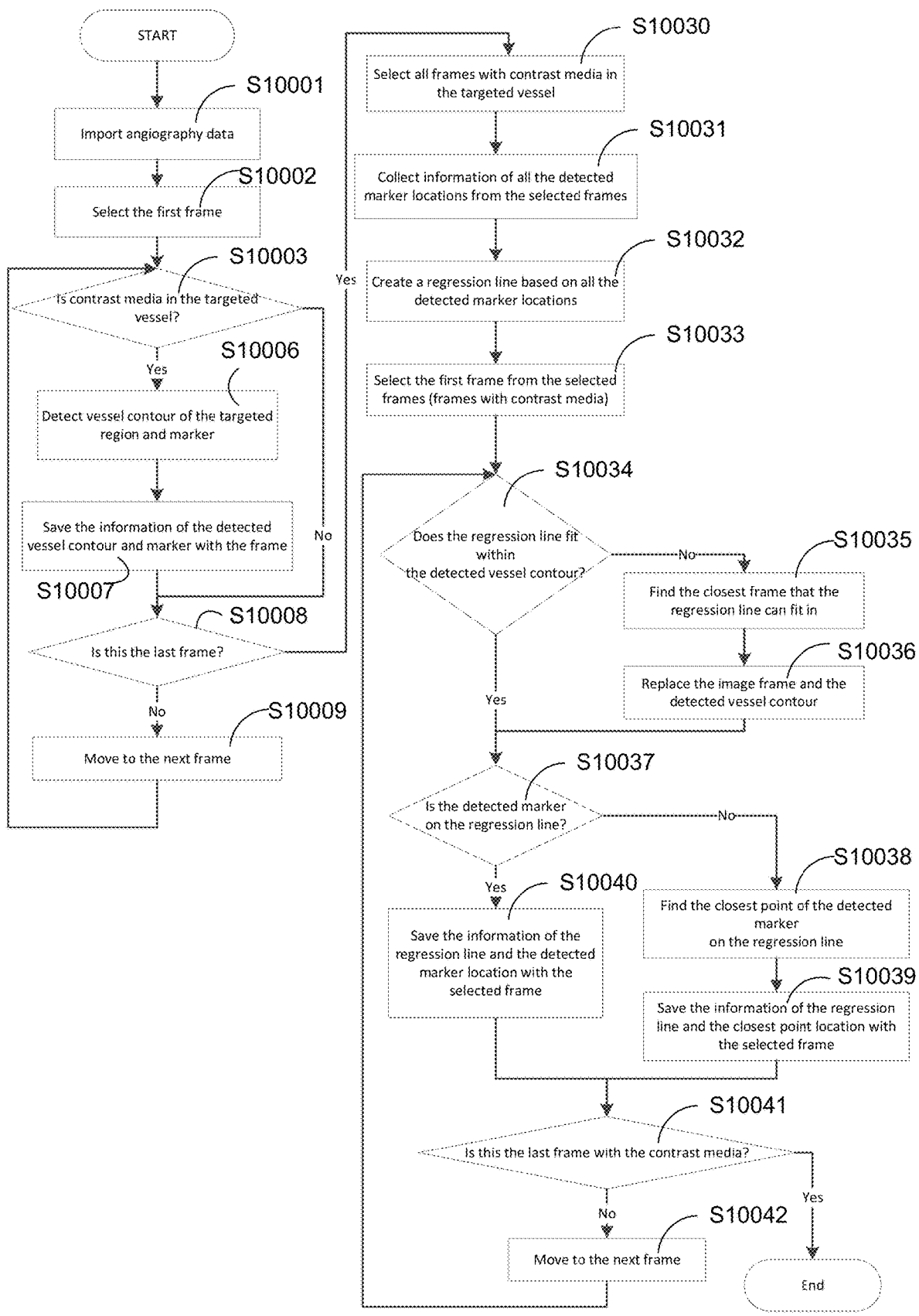
Figure 10D:
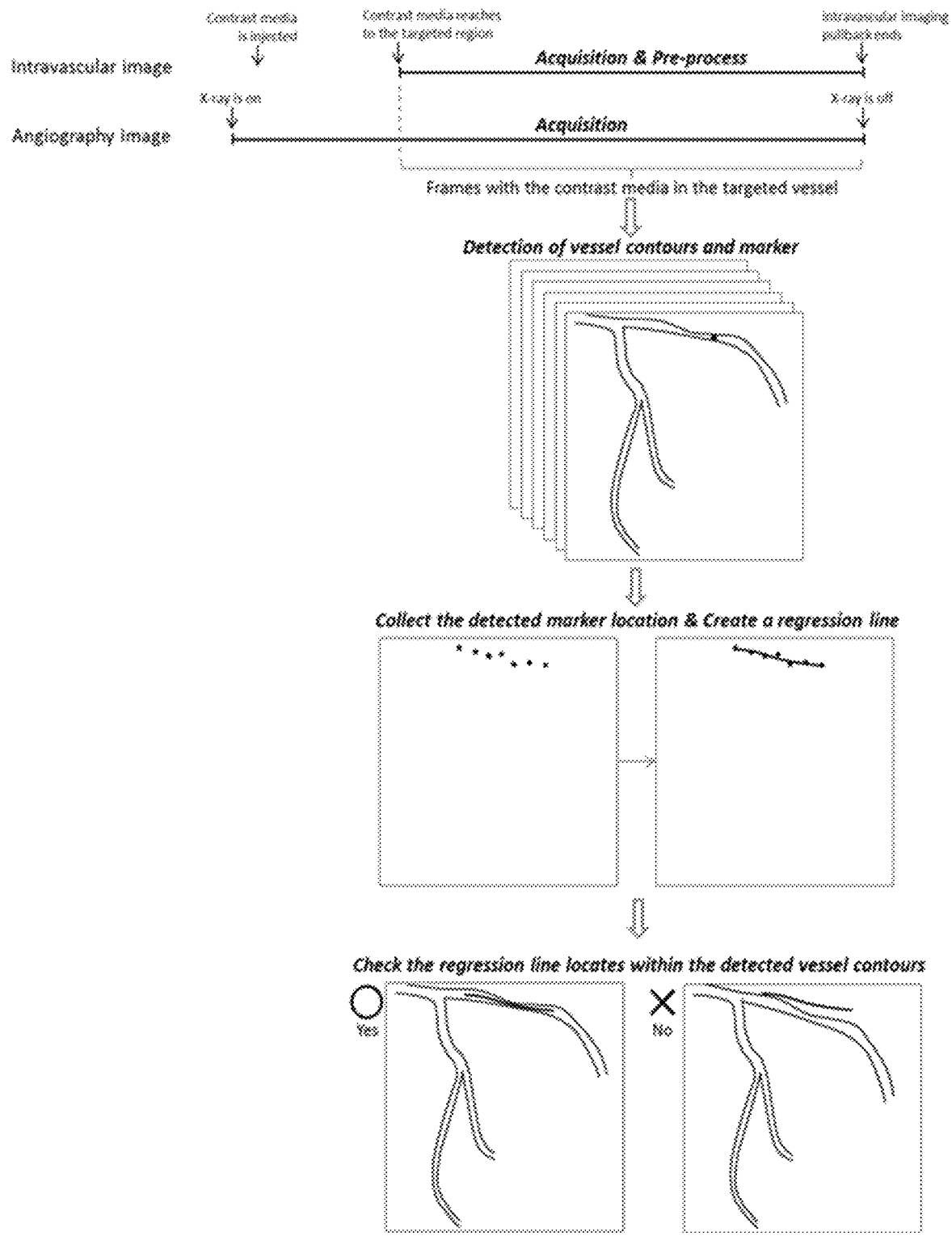

FIG. 9 describes an embodiment of an overall workflow of coregistration (e.g., an embodiment example of one or more steps of the "Coregister" subprocess box step S1006 shown in FIG. 1). In one or more embodiments, a method may include acquiring an intravascular image (see e.g., step S9001 in FIG. 9), and may include acquiring an angiography image simultaneously to, before, or after the intravascular image (see e.g., step S9002 in FIG. 9). The detailed workflow of the first 3 steps of coregistration (import angiography image (see e.g., step S9003 in FIG. 9), detect a marker location (see e.g., step S9004 in FIG. 9), and create a coregistration path (see e.g., step S9005 in FIG. 9) is described in FIG. 10 (which includes FIGS. 10A-10D discussed below). As described in the previous paragraph, since an imaging catheter path may be used as a coregistration path, the accuracy of coregistration may depend on the accuracy of an imaging catheter path generation. After importing an angiography image to the system (see e.g., step S9003 in FIG. 9), the system checks whether the cardiac phase information is associated with the imported angiography image. If so, the system checks whether the imported angiography image has enough or a sufficient number of frames (e.g., above a predetermined number or threshold, available for a predetermined amount of time, etc.) without the contrast media in the predetermined area (e.g., the targeted vessel (i.e., the vessel region where the intravascular image is acquired)). The one or more criterion for the number of frames may be determined in relation to a cardiac cycle. The system judges that the number of frames is sufficient if (or in a case where) the angiography frames without the contrast media are available for at least one cardiac cycle. This checking process may be assisted by a user as needed. Based on these two pieces of information (i.e., the availability of cardiac phase information and the availability of a number of angiography frames without the contrast media), the system may automatically select either of the following processes of a coregistration path generation. FIG. 10A and FIG. 10B (which shows at least one embodiment example description of FIG. 10A) show a case when the angiography image has the cardiac phase information (e.g., the angiography data is synchronized with an ECG signal) and when there is enough or a sufficient number of angiography frames without the contrast media in the predetermined area (e.g., the targeted vessel). In this case, the system can directly detect a coregistration path (e.g., an imaging catheter path). Detection accuracy may be improved by the effect of cardiac motion with the usage of the cardiac phase information and by checking the detected imaging catheter path location with the detected marker location. FIG. 10C and FIG. 10D (which shows at least one embodiment example description of FIG. 10C) show a case when the angiography image does not have the cardiac phase information and/or when there is not enough or a sufficient number of angiography frames without the contrast media in the targeted vessel. In this case, a coregistration path (e.g., an imaging catheter path) is hard to be detected directly from each angiography frame. Therefore, the system generates the coregistration path or imaging catheter path accurately by using the detected marker location. In one or more embodiments, a coregistration method may include finding a location where each intravascular image is acquired on an angiography image (see e.g., step S9006 in FIG. 9), and may include displaying information (such as the location) to a GUI (see e.g., step S9007 in FIG. 9).

Figure 11:
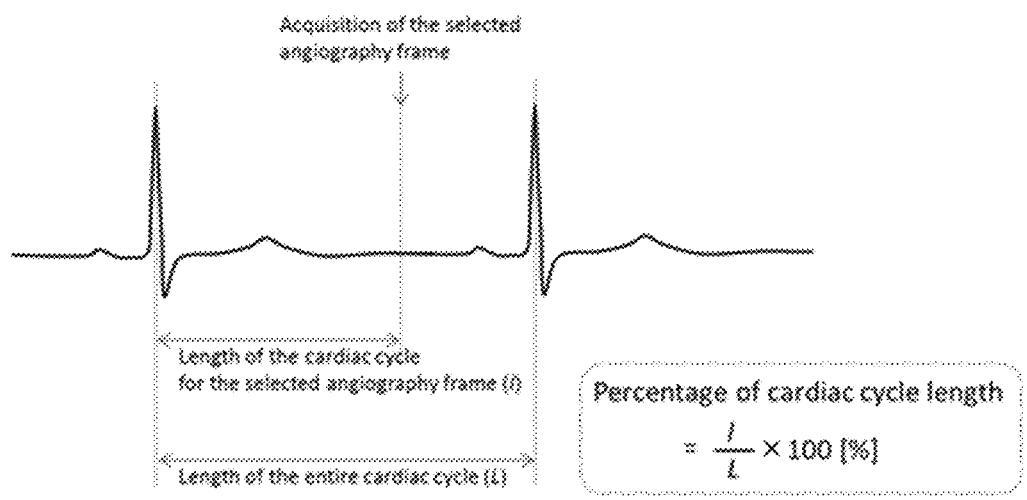
FIG. 11 shows at least one embodiment example of how to evaluate cardiac phase information in accordance with one or more aspects of the present disclosure.

Looking closer at the case(s) of FIGS. 10A-10B, first the acquired and/or imported angiography frames (see e.g., step S1000i in FIG. 10A) are preferably split into two groups by selecting each frame for evaluation (see e.g., step S10002 in FIG. 10A through step S10009 to move to a next frame in FIG. 10A until a last frame is reached (see e.g., step S10008 in FIG. 10A)): (1) the frame without the contrast media in the targeted vessel (the frames that are captured before the contrast media reached to the intravascular imaging region) (see e.g., "No" in step S10003 in FIG. 10A), and (2) the frame with the contrast media in the targeted vessel (see e.g., "Yes" in step S10003 in FIG. 10A). Then, an imaging catheter path may be detected from each angiography frame in Group (i) (see e.g., at least step S10017 and/or S10018 in FIG. 10A), and vessel contours and a radiopaque marker on the imaging catheter may be detected from each angiography frame in Group (2) (see e.g., steps S10006 and S10007 in FIG. 10A). As an example, a guidewire over which the imaging catheter is delivered to the targeted vessel or a drive-cable of the imaging catheter may be used as the imaging catheter path. The imaging catheter path and the vessel contours can be detected by applying an edge detection filter, such as Sobel, Canny, Prewitt, Roberts, Kernel, Laplacian of Gaussian, or others, and/or any combination from these. The radiopaque marker can be detected with, for example, Viterbi-based method, and/or any machine learning or deep learning-based method. The detected information is saved to each angiography frame with the cardiac phase information. The cardiac phase information is obtained based on an ECG signal. One way to evaluate the cardiac phase information is calculating the percentage of cardiac cycle length (see FIG. 11 showing at least one embodiment example of how to evaluate the cardiac phase information). After the processes of detecting and saving for entire angiography frames (see e.g., steps S10002 for selecting a first frame, S10003 to determining whether a contrast media is in a target (e.g., a targeted vessel), S10004 for detecting an intravascular imaging catheter path in a case with no contrast media, S10005 for saving the information of the detected catheter path and its cardiac phase with the frame in a case with no contrast media, S10006 for detecting a vessel contour of a targeted region and marker in a case with contrast media, S10007 for saving the information of the detected vessel contour, marker, and its cardiac phase with the frame in the case with contrast media, S10008 to check whether the evaluated frame is the last frame or not, S10009 to move to the next frame in a case where the evaluated frame is not the last frame, etc. in FIG. 10A), the system chooses one angiography frame from Group (2) (see e.g., step S10010 in FIG. 10A) and finds an angiography frame with the same cardiac phase in Group (1) (see e.g., step S10011 in FIG. 10A). Then, the imaging catheter path detected in the angiography frame selected from Group (i) is overlaid on the angiography frame selected from Group (2) (see e.g., step S10012 in FIG. 10A). Using this overlaid image, the system determines or evaluates whether the detected marker is located or is disposed on or within a certain distance from the detected imaging catheter path (see e.g., one or more of: step S10013 for determining whether a detected catheter path is located within a detected vessel contour; step S10014 for determining whether the detected marker location is on the catheter path in a case where the detected catheter path is located within the detected vessel contour; step S10015 for determining whether the detected marker location is close enough to the catheter path in a case where the detected marker location is not on the catheter path; step S10016 for determining whether there is another frame without contrast media at the same cardiac phase in a case where the detected marker location is not close enough to the catheter path and, if so, return to step S10012 or, if not, proceed to step S10019; or in a case where the detected marker location is close enough to the catheter path in step S10015, then proceed to step S10017 to find a closest point on the catheter path and update the marker location and then proceed to step S10018 to save the information of the catheter path location with the selected angiography frame with contrast media, as well as the detected/updated marker location; or in a case where the detected marker location is on the catheter path in step S10014, then proceed directly to step S10018 as shown in FIG. 10A). The threshold of the distance may be pre-determined by the system or determined by a user. If the overlaid image meets both criteria, the information of the detected catheter path location is saved with the angiography frame selected from Group (2) (see e.g., step S10018 in FIG. 10A). When the detected marker is not located or disposed on the detected imaging catheter path but is located or disposed within a certain distance (see e.g., "Yes" in step S10015 in FIG. 10A), the closest location to the detected marker location on the imaging catheter path is searched (see e.g., step S10017 in FIG. 10A), and its location is saved with the angiography frame selected from Group (2) by updating the detected marker location (see e.g., step S10018 in FIG. 10A). The system may also check whether the detected imaging catheter path is located or disposed between or within the detected vessel contours (see e.g., step S10013 in FIG. 10A) to make sure the detected imaging catheter path may be a representative line of the vessel's longitudinal direction. If the overlaid image does not meet either one of the criteria, the system searches another angiography frame in Group (i) and follows the same processes (see e.g., step S10016 in FIG. 10A). If there is no other angiography frame in Group (i) with the same cardiac phase, the system stops the processes for the angiography frame selected from Group (2) (see e.g., "No" in step S10016 in FIG. 10A). Then, the system selects another frame in Group (2) (see e.g., "No" in step S10019 and step S10020 in FIG. 10A) and repeats the entire set of processes (see e.g., step S10020 returning to step Sworn in FIG. 10A) until the last frame in Group (2) is processed (see e.g., "Yes" in step S10019 in FIG. 10A).

Looking closer at the case(s) of FIGS. 10C-10D, first the angiography frames with the contrast media in the targeted vessel preferably are selected (see e.g., steps Sworn through S10009 in FIG. 10C; steps similarly numbered as steps shown in FIG. 10A may have the same or similar processes or may differ in one or more ways as discussed below) (see also, step S10030 in FIG. 10C), and the radiopaque marker and the vessel contours preferably are detected for each selected angiography frame (see e.g., step S10031 in FIG. 10C). Then, all the information of the detected radiopaque marker locations may be collected (see e.g., step S10031 in FIG. 10C) and plotted in the same plane. Based on the detected marker locations, a regression line may be created (see e.g., step S10032 in FIG. 10C) by using, for example, least squares regression method(s). After that, the system selects an angiography frame from the previously selected angiography frames (see e.g., step S10033 in FIG. 10C) and checks whether the regression line is located or disposed within the detected vessel contours (see e.g., step S10034 in FIG. 10C). If the regression line is located or disposed within the contours, then the process proceeds to step S10037 discussed below. If the regression line is not located or disposed within the contours ("No" in step S10034 in FIG. 10C), the system searches another angiography frame that may have the regression line located within the contours and that may be acquired at the closest timing to the original one (see e.g., step S10035 in FIG. 10C). Then, the searched angiography frame is used (or replaced) as the angiography frame that is captured at the timing of the originally selected angiography frame (see e.g., step S10036 in FIG. 10C). At this replacement of the angiography frame, the information of the detected vessel contours should be replaced with the one of the searched angiography frame, while the information of the detected marker location should not be replaced, in one or more embodiments, to the one of the searched angiography frame because the detected marker location is the true location of the radiopaque marker on the imaging catheter or probe at that timing. To show the coregistration path on each angiography frame in a meaningful manner, in one or more embodiments, the path should be or is preferably located within the vessel contour. By replacing the angiography frame in which the coregistration path is not located within the vessel contour to the angiography frame in which the coregistration path is located within the contour and that is captured at the closest timing, all the frames that would be displayed on the GUI should or preferably have the coregistration path within the vessel. Then, the system checks whether the detected marker is located or disposed on the regression line (see e.g., step S100037 in FIG. 10C). If the detected marker is located or disposed on the regression line, then the information of the regression line and the detected marker location is saved with the frame (see e.g., step S10040 in FIG. 10C). If the detected marker is not located or disposed on the regression line (see e.g., "No" in step S10037 in FIG. 10C), the system searches the closest location to the detected marker location on the regression line (see e.g., step S10038 in FIG. 10C), and updates the information of the marker location with the newly searched location. After that, the information of the detected or updated marker location and the regression line is saved with the selected angiography frame (see e.g., step S10039 in FIG. 10C). These processes are repeated for the entire set of angiography frames with the contrast media in the targeted location (e.g., the targeted vessel) (e.g., until the last frame with the contrast media is detected (see e.g., in step S10041 in FIG. 10C)). If a frame is not the last frame, then the process proceeds to the next frame (see e.g., step S10042 in FIG. 10C). The processes after creating a regression line may be performed in a different order. For example, the system first may check whether the regression line is located or disposed within the detected vessel contours and may update the angiography frame if necessary for the entire set of angiography frames. Then, the system may check whether the detected marker is located or disposed on the regression line or not and updates the location of the detected marker if necessary.

Figure 12A:
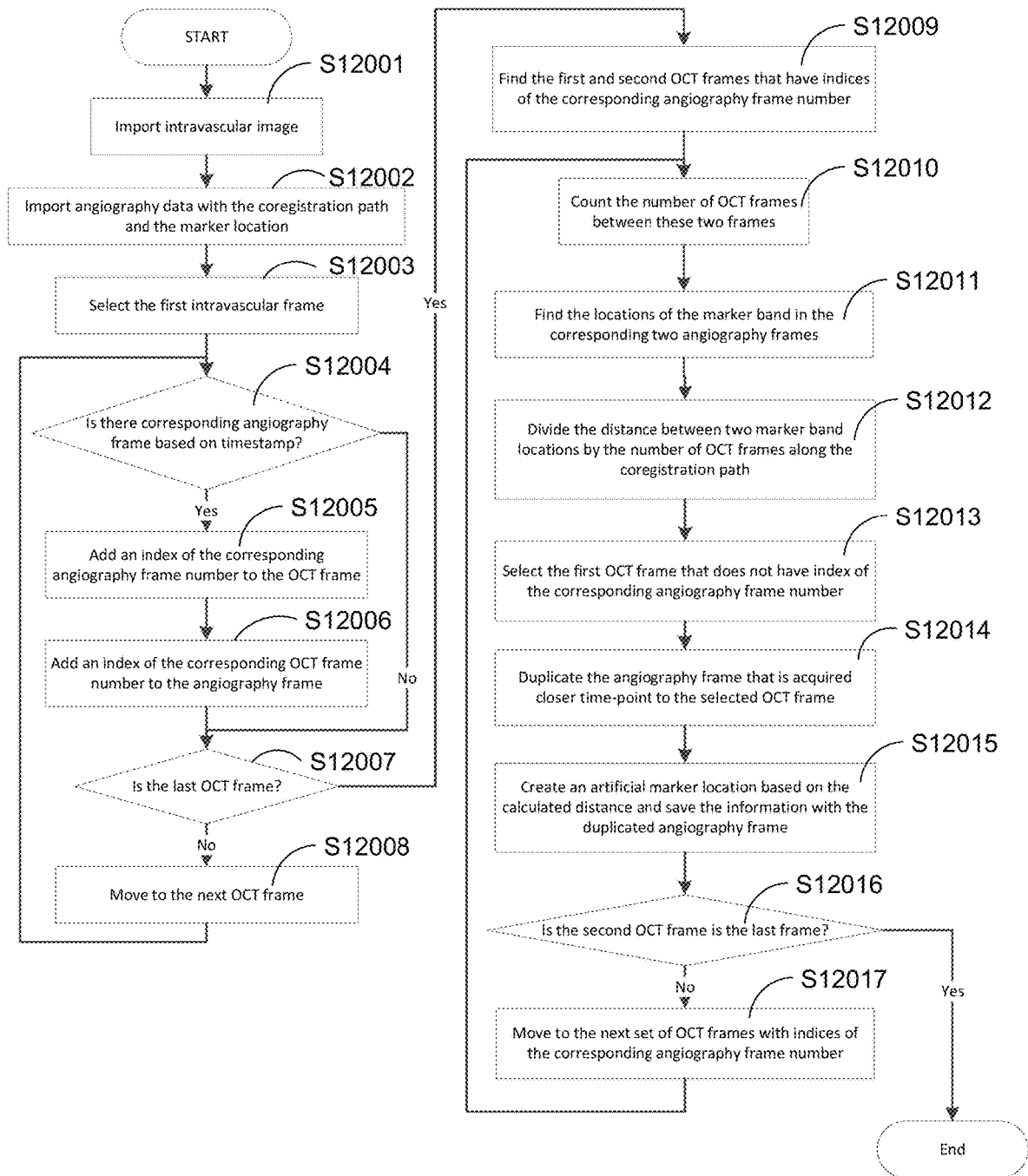
FIGS. 12A-17 describe one or more detailed steps of coregistration for each option of one or more options in accordance with one or more aspects of the present disclosure.
Figure 12B:
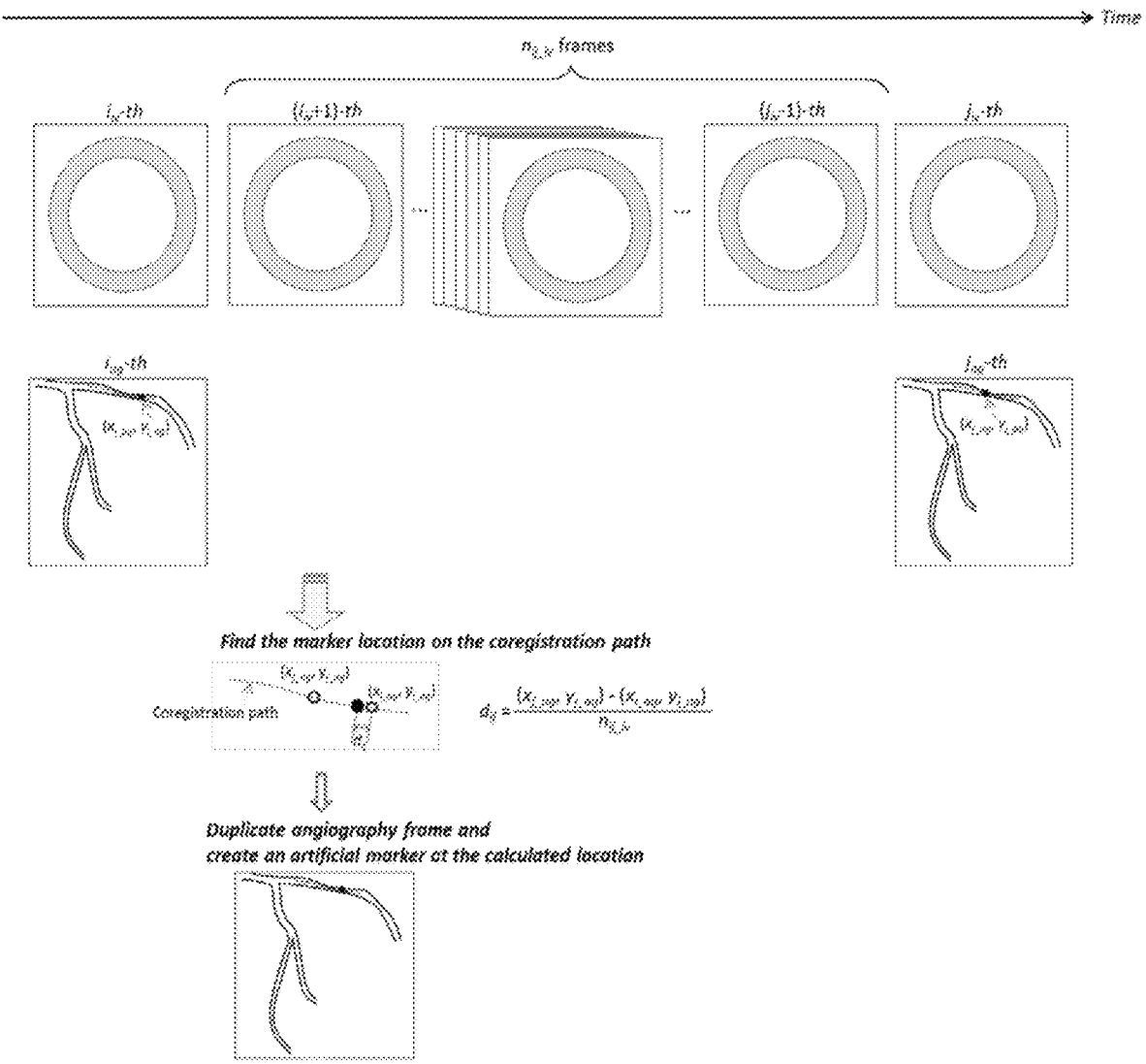

FIG. 12 (which includes FIGS. 12A-12B) describes the details of the fourth step of one or more embodiments of coregistration (find an acquisition location of each intravascular image frame; see FIG. 12A for a detailed workflow embodiment of at least one example of the fourth step of coregistration, and see FIG. 12B for a visual description of FIG. 12A). From previous steps that are described in the previous paragraph(s), the system has the intravascular image and the angiography image with the coregistration path, either the directly detected imaging catheter path or the newly generated imaging catheter path with, for example, the regression model, and the detected marker locations. While an intravascular image may be an OCT image, such images are not limited to OCT, which is a non-exhaustive, non-limiting embodiment example. Intravascular image data may be imported (see e.g., step S12001 in FIG. 12A), and angiography data with a coregistration path and a marker location data may be imported (see e.g., step S12002 in FIG. 12A). A first intravascular image may be selected (see e.g., step S12003 in FIG. 12A). In one or more embodiments, the system preferably searches the intravascular frames that have the angiography frames taken at the same time using the timestamps of both the intravascular image and the angiography image (see e.g., step S12004 in FIG. 12A). Then, indices of the corresponding angiography frame number are added to each of the selected intravascular frames (see e.g., step S12005 in FIG. 12A), while the indices of the corresponding intravascular frame number are added to each of the angiography frames (see e.g., step S12006 in FIG. 12A). The process (e.g., steps S12004 through S12008 in FIG. 12A) is repeated for each intravascular image until the intravascular image frame is the last (see e.g., determination of step S12007 in FIG. 12A). After that, the system preferably finds the first and second intravascular frames [$i_{iv}$-th and $j_{iv}$-th frames] that have the indices of the corresponding angiography frame number (see e.g., step S12009 in FIG. 12A), and counts the number of intravascular frames between these two selected frames [$n_{ij\_iv}=j_{iv}-i_{iv}$] (see e.g., step S12010 in FIG. 12A). Then, the system finds the corresponding marker locations [($x_{i\_ag}$, $y_{i\_ag}$) and ($x_{j\_ag}$, $y_{j\_ag}$)] from the corresponding angiography frames [$i_{ag}$-th and $j_{ag}$-th frame] (this is at least one example of an embodiment of step S12011 in FIG. 12A). Next, the system divides the distance between ($X_{i\_ag}$, $y_{i\_ag}$) and ($x_{j\_ag}$, $y_{j\_ag}$) by $n_{ij\_iv}$ along the coregistration path [$d_{ij}=\{(x_{j\_ag}, y_{j\_ag})-(x_{i\_ag}, y_{i\_ag})\}n_{ij\_iv}$] (this is at least one example of an embodiment of step S12012 in FIG. 12A). After that, the system selects the ($i_{iv}$+1)-th intravascular frame (this is at least one example of an embodiment of step S12013 in FIG. 12A) and duplicates the angiography frame that is acquired at the closer or closest timing on which the ($i_{iv}$+1)-th intravascular frame is acquired (this is at least one example of an embodiment of step S12014 in FIG. 12A). When the angiography frame is duplicated, the imaging catheter path is also duplicated in one or more embodiments. On the duplicated angiography frame, the system creates a point (e.g., an artificial marker) that is located at the calculated distance $d_{ij}$ from ($x_{i\_ag}$, $y_{i\_ag}$) along the coregistration path. The system then saves the point or artificial marker location on the duplicated angiography frame with the index of the corresponding intravascular frame number (see e.g., step S12015 in FIG. 12A). The system repeats these processes until the system finishes the processes for the ($j_{iv}$−1)-th intravascular frame (see e.g., step S12016 determining whether the second frame is the last frame as shown in FIG. 12A, and the moving to the next set of intravascular frames with indices of the corresponding angiography frame number in a case where "No" results from step S12016 as shown in step S12017 in FIG. 12A). Then, the system finds the second and the third intravascular frames that have the indices of the corresponding angiography frame number, and repeats all the processes that are described above in one or more embodiments. These processes (e.g., steps S12010 through S12017 as shown in FIG. 12A) repeat until the system finishes the subject processes for the second to last (penultimate) and the last intravascular frames that have the indices of the corresponding angiography frame number (see e.g., step S12016 of FIG. 12A). Entire processes that are described in this paragraph may be done in a different order, and such processes are not limited to the order or to using all of the steps of FIG. 12A. For example, the system may create the points or artificial markers every time when the system finds two intravascular frames that have angiography frames that are acquired at the same time-points.

Additionally or alternatively, there is another method embodiment that may be used to create a coregistration pair between the intravascular image and the angiography data. In the description above, when the ($i_{iv}$+1)-th intravascular frame is selected, the angiography frame is duplicated. But in another method embodiment, the angiography frame does not have to be duplicated. When the ($i_{iv}$+1)-th intravascular frame is selected, the angiography frame that is acquired at the closest timing on which the ($i_{iv}$+1)-th intravascular frame is acquired is searched, and its frame number is saved to the index of the ($i_{iv}$+1)-th intravascular frame. Then, the acquisition location of the ($i_{iv}$+1)-th intravascular frame is searched on the coregistration path using the same processes described in the previous paragraph(s). The searched location may be saved to the ($i_{iv}$+1)-th intravascular frame, along with the index of the angiography frame number.

Figure 13:
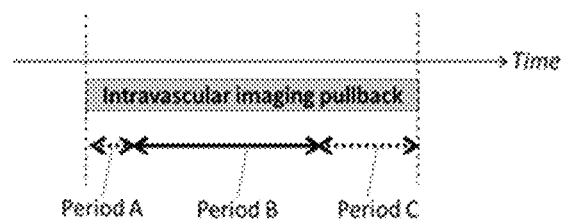
Figure 14:
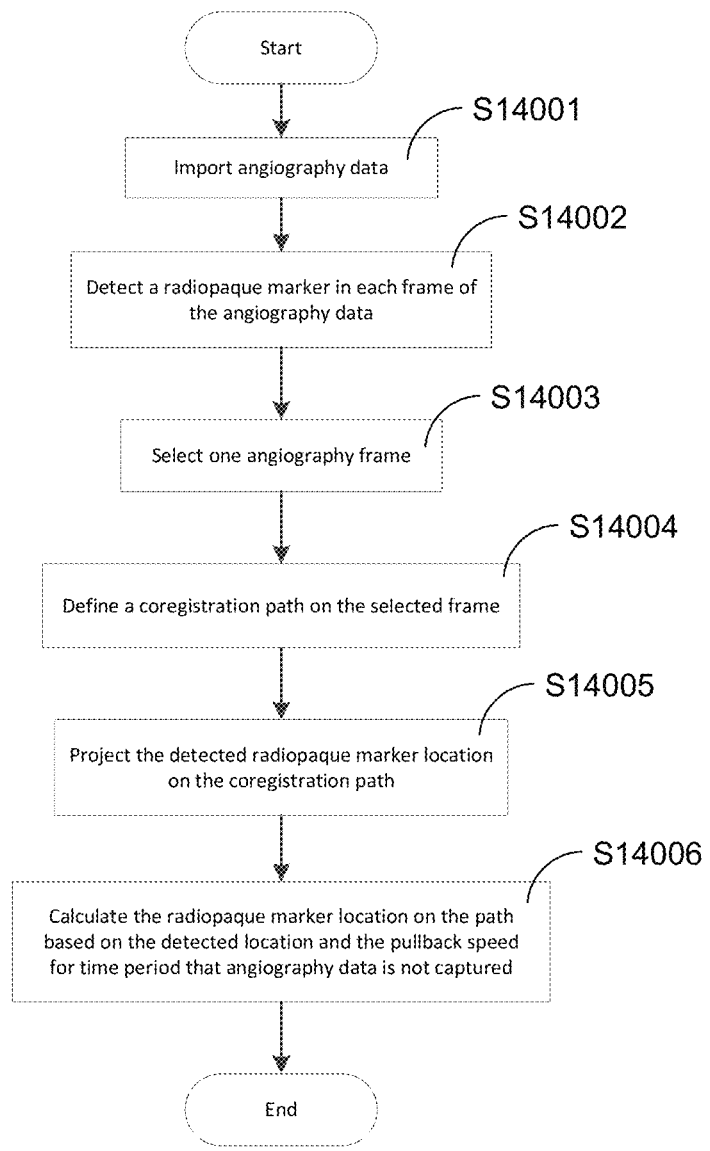

For one or more embodiments of Option 3 303 (see e.g., FIG. 3), FIG. 13 is a schematic figure to describe when the angiography image is captured during (or relative to) intravascular imaging pullback. In the embodiment of FIG. 13, period B is the time period when the angiography image is captured and available, and periods A and C are the time periods when the angiography image is not captured and not available. FIG. 14 is a flowchart of at least one embodiment example for performing coregistration for option 3 (see element 303 of FIG. 3). One or more embodiments of FIG. 14 also may focus on the first 3 steps of coregistration in FIG. 9. The $4^{th}$ step of one or more coregistration embodiments may be performed in the same manner that is described above. After importing the angiography data (see e.g., step S14001 in FIG. 14), first, the radiopaque marker may be detected (see e.g., step S14002 in FIG. 14) in period B in the similar way to Option 1 301 or Option 2 302. Then, the system selects one angiography frame (see e.g., step S14003 in FIG. 14) and defines a coregistration path (see e.g., step S14004 in FIG. 14). This path may be a vessel centerline or an imaging catheter path. Then, the detected radiopaque marker locations are projected onto the coregistration path (see e.g., step S14005 in FIG. 14). Based on these projected locations in period B, the radiopaque marker locations in period A and period C may be calculated along the extracted coregistration path using the pullback speed of the intravascular imaging (see e.g., step S14006 in FIG. 14). If the system calculates the acquisition locations of intravascular image(s) based on the detected radiopaque marker locations during period B before a coregistration path is defined or before the locations are projected onto the path, the acquisition locations for periods A and C may be calculated at the later steps in one or more additional or alternative embodiments.

For one or more embodiments of Option 4 304 (see e.g., FIG. 3), since the angiography image is available from two or multiple angles, coregistration may be performed in 3D space.

Figure 15:
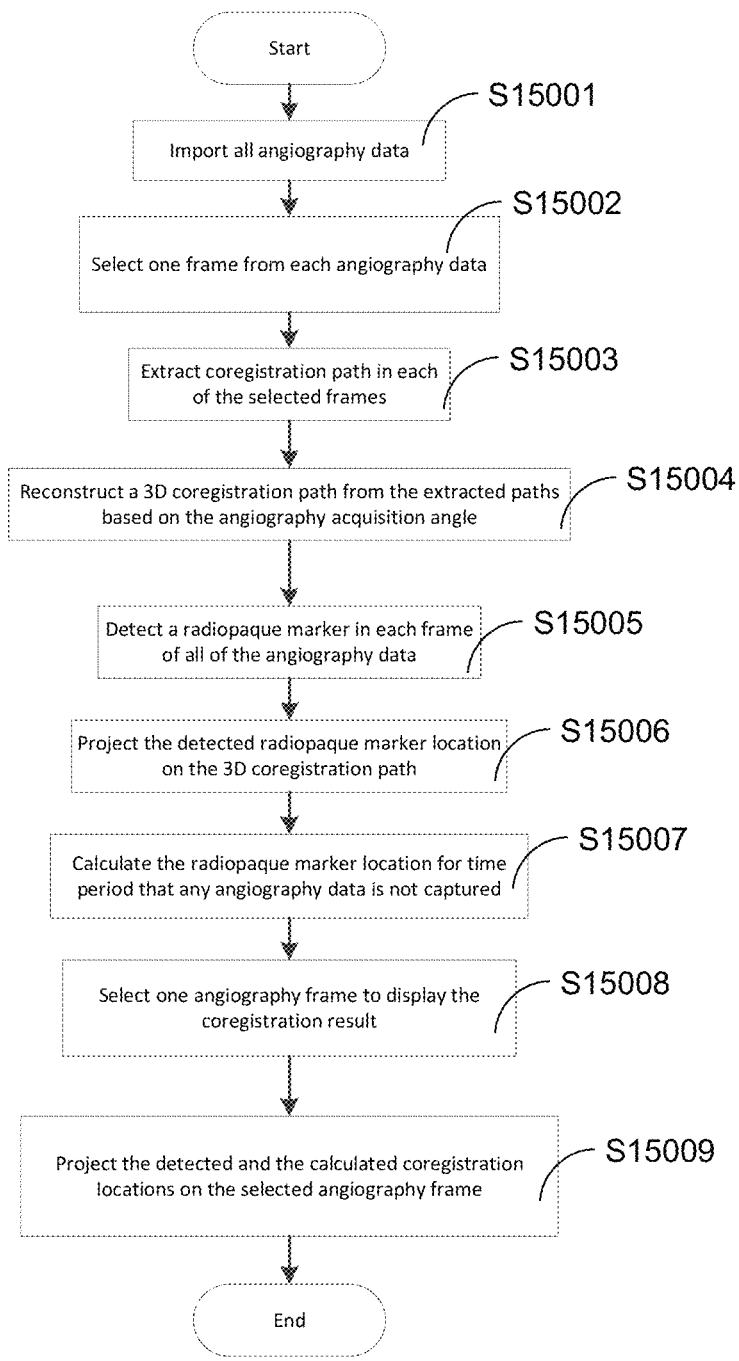

FIG. 15 shows a flowchart of one embodiment example of coregistration for Option 4 (see e.g., element 304 in FIG. 3). As same as or similar to other options, this flowchart describes processes for the first 3 steps in FIG. 9 that may be used in one or more embodiments (regardless of whether reference numbers are the same or not). The last step may be performed in the same way that is described above. After importing all the angiography data to the system (see e.g., step S15001 in FIG. 15), as a first step, one frame is preferably selected from each angiography data (see e.g., step S15002 in FIG. 15). The selection may be automatic, for instance using an ECG signal if available, or may be manual by a user. Then, the system extracts a coregistration path, e.g., a vessel centerline or an imaging catheter path, from each of the selected frames (see e.g., step S15003 in FIG. 15). Then, the system reconstructs a 3D coregistration path from the extracted paths with or using, for instance, stereoscopic theory, using the acquisition angle of angiography, e.g., C-arm angle (the acquisition angle for or in the C-arm shown in, for example, FIG. 2) (see e.g., step S15004 in FIG. 15). After that, the system detects a radiopaque marker in each frame of all the angiography data in the same way that is described in Options 1-3 (see e.g., elements 301-303 in FIG. 3) (see e.g., step S15005 in FIG. 15). These locations are then projected onto the reconstructed 3D coregistration path (see e.g., step S15006 in FIG. 15). As same as or similar to Option 3 (see e.g., element 303 in FIG. 3), if (in a case where) the system calculates acquisition locations from the detected radiopaque marker locations, the acquisition locations may be used instead of radiopaque marker locations in the further processes. After projecting the detected locations onto the 3D coregistration path, the radiopaque marker locations are calculated for the time period that any angiography data is available in the same way that is described in Option 3 (see e.g., element 303 in FIG. 3) (see e.g., step S15007 in FIG. 15). Then, one angiography frame is selected to display the coregistration result (see e.g., step S15008 in FIG. 15). The system may automatically select a frame or a user may select a frame (e.g., manually). After the selection, all the detected or the calculated coregistration locations, e.g., the locations where the intravascular image is acquired, are projected onto the selected angiography frame (see e.g., step S15009 in FIG. 15).

Figure 16:
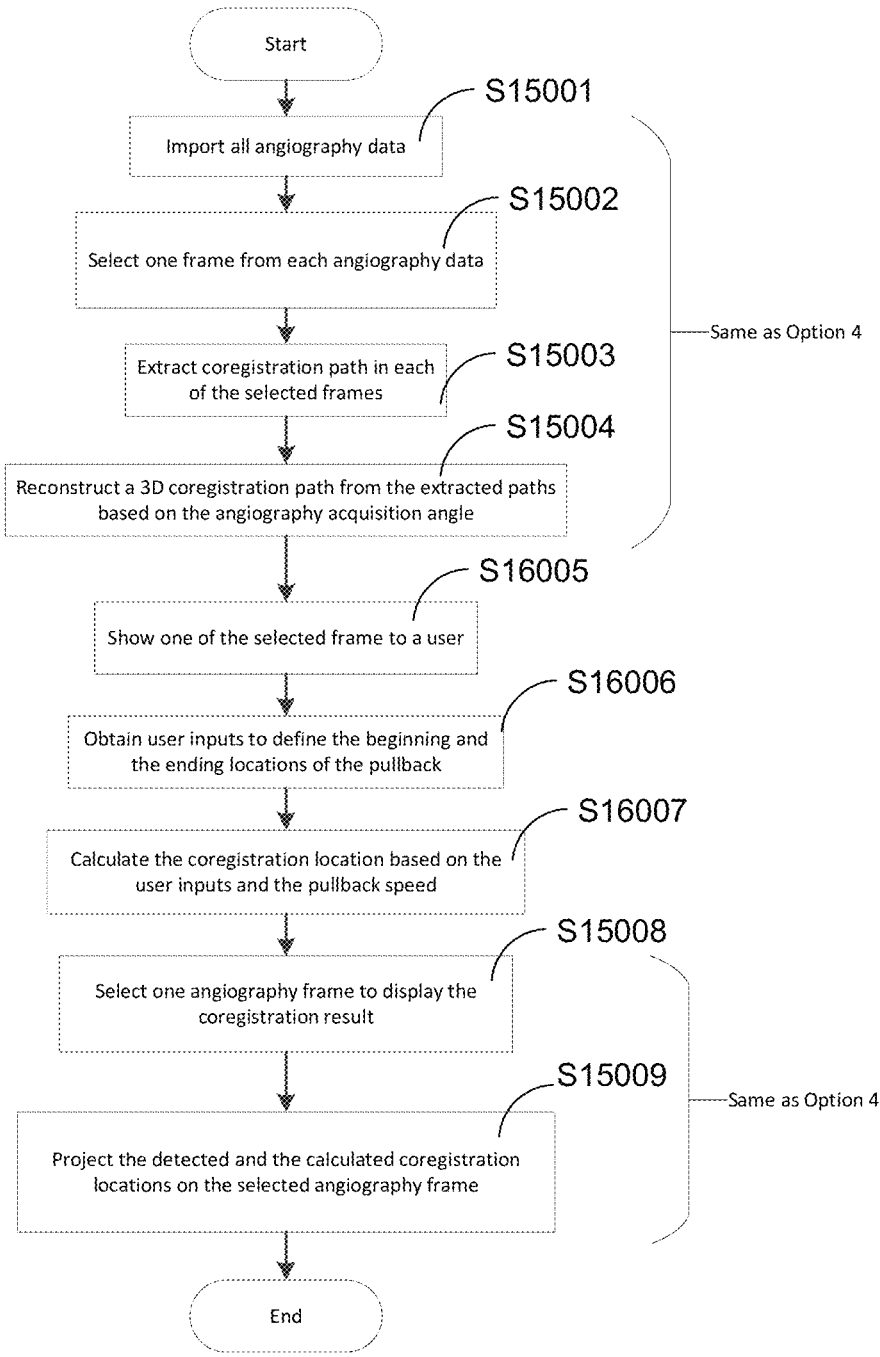

For one or more embodiments of Options 5/5' and/or 6/6' (see e.g., elements 305/305' and/or 306/306', respectively, in FIG. 3), as same as or similar to Option 4 (see e.g., element 304 in FIG. 3), coregistration may be performed in 3D space. FIG. 16 shows a flowchart of one embodiment example of coregistration for these options. As same as other options, this flowchart describes processes for the first 3 steps in FIG. 9.

In FIG. 16 (which shows a flowchart that may be used for any of Options 5, 5', 6, and/or 6' (see e.g., elements 305, 305', 306, and/or 306', respectively, in FIG. 3), the first 4 steps (see e.g., steps S15001-S15004 in FIG. 16) are the same as those used in or for Option 4 (see e.g., steps S15001-S15004 in FIG. 15). For Options 6 and 6' (see e.g., elements 306 and 306' in FIG. 3), the second step (select one frame from each angiography data) may be skipped since only one angiography frame is available for each angiography acquisition angle. For Options 5 and 6 (see e.g., elements 305 and 306 in FIG. 3), if (in a case where) one or both of the angiography data are captured before the contrast media injection, an imaging catheter path may be extracted as a coregistration path (see e.g., step S15003 in FIG. 16). After extracting the coregistration paths, the system reconstructs a coregistration path in 3D space based on the extracted paths and the acquisition angles (see e.g., step S15004 in FIG. 16). Next, one angiography frame is selected. This selection may be automatic by the system or may be manual by a user. Then, the system shows this frame (see e.g., step S16005 in FIG. 16) and asks a user to place locations where the pullback starts and ends on the frame (see e.g., step S16006 in FIG. 16). Based on these user inputs and the pullback speed, the coregistration locations may be calculated on the 3D coregistration path (see e.g., step S16007 in FIG. 16). After the calculation, as same as in Option 4 (see e.g., element 304 in FIG. 3; see also, steps in FIG. 15), the system or a user selects one angiography frame to display the coregistration result (see e.g., step S15008 in FIG. 15 or FIG. 16), and the system projects the calculated coregistration locations onto the selected angiography frame (see e.g., step S15009 in FIG. 15 or FIG. 16). The frame that is previously selected for user inputs may be selected again for this step if a user prefers.

Figure 17:
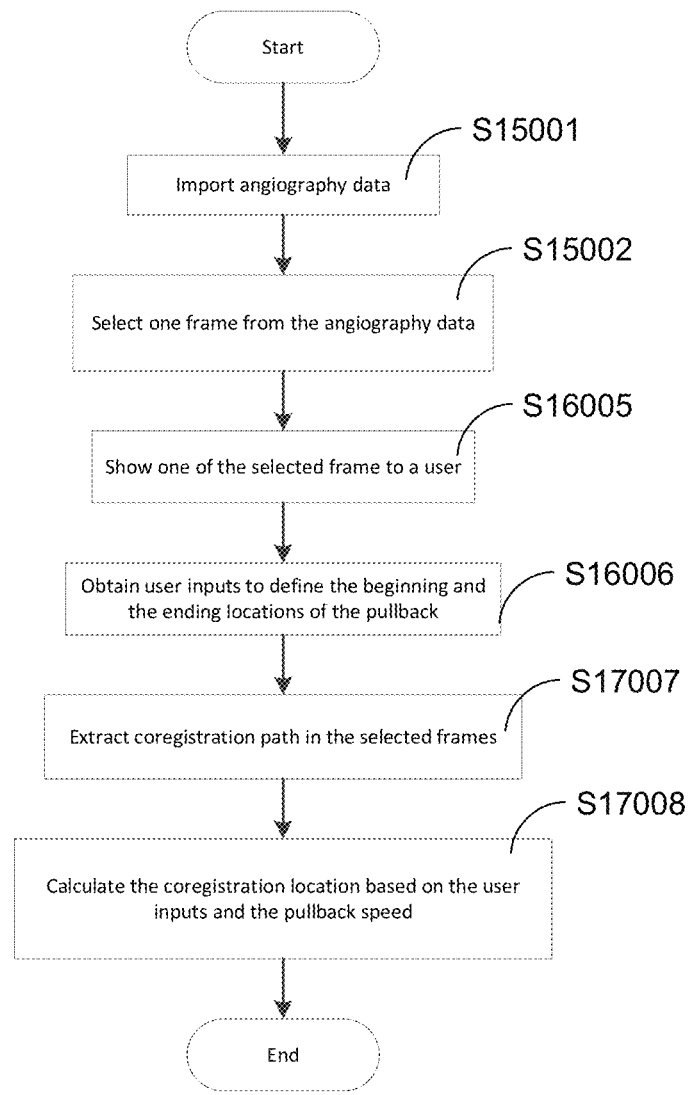

For one or more embodiments of Option 7 (see e.g., element 307 in FIG. 3), FIG. 17 shows a flowchart of one embodiment example of a coregistration method. As same as other options, this flowchart describes processes for one or more embodiments of the first 3 steps in FIG. 9. In this option, if (in a case where) the angiography data contains multiple frames, one angiography frame is first selected (see e.g., step S15002 in FIG. 17). This selection may be automatic by the system or may be manual by a user. In one or more embodiments, the selected frame may be shown to a user (see e.g., step S16005 in FIG. 17). Then, a user is asked to place inputs at the beginning and the ending locations of the pullback on the selected frame (see e.g., step S16006 in FIG. 17). After that, the system extracts a coregistration path in the selected frames (see e.g., step S17007 in FIG. 17) and calculates the coregistration locations on the extracted path (see e.g., step S17008 in FIG. 17). The extraction may be performed before the system obtains user inputs in one or more embodiments.

If a user prefers, two or more views of angiography data may be captured for coregistration for Option7 (see e.g., element 307 in FIG. 3). If that is the case, the coregistration may be performed in the similar manner to Options 5' or 6' (see e.g., element 305' or 306', respectively, in FIG. 3).

If another imaging (mode or method) that can show coronary artery anatomy globally, such as CT angiography, is available, and if a user prefers to use this imaging data instead of acquiring additional angiography data, similar processes of Option 7 can be performed. Since, in most cases, CT angiography data may create a 3D structure of coronary artery anatomy, a user preferably selects a viewing plane (2D plane). A user can select the 2D plane that is similar to the angle of other angiography data that is captured during the PCI procedure. If a user prefers, this selection may be done automatically by an apparatus or system in one or more embodiments. The automatic selection may be performed by setting a default viewing angle by a user or by selecting the viewing angle to make it closer to that of the other available angiography data during the same procedure. After that, same processes for Option 7 (see e.g., element 307 in FIG. 3) may be performed and a coregistration result(s) can be shown to a user.

If a user prefers to perform coregistration in 3D, the same processes for Option 5/5' or 6/6' (see e.g., element 305/305' or 306/306', respectively, in FIG. 3) can be performed.

If other angiography imaging data prior to the intravascular pullback is available, and if a user prefers to use that image, the same processes for Option 7 (see e.g., element 307 in FIG. 3) may be performed, and a coregistration result(s) can be shown to a user.

Figure 18:
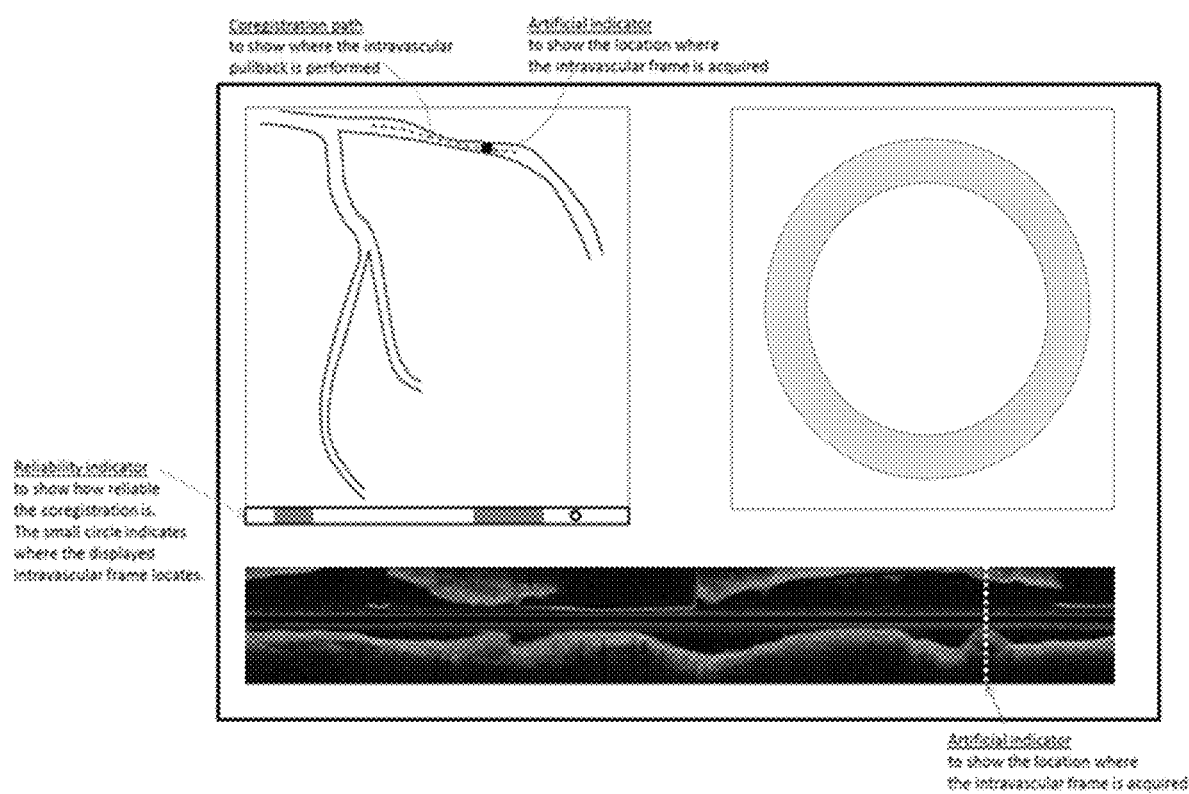
FIG. 18 shows at least one embodiment example of displaying coregistration result(s) in accordance with one or more aspects of the present disclosure.

The final step of coregistration is displaying the result on or to the display or monitor. The result may be displayed on the monitor that is connected to the intravascular system and/or the monitor that is connected to the angiography system. After the previous steps, the system has the intravascular image and the angiography image with the corresponding intravascular frame number. Once an intravascular frame is selected by the system or by a user, the system searches the corresponding angiography frame using the indices of the angiography image and displays the angiography frame on the monitor with an artificial indicator overlaid on the angiography frame. This artificial indicator shows the position where the selected intravascular frame is acquired, which is directly found or calculated as described in the previous paragraph(s). The system also overlays the coregistration path (e.g., the imaging catheter path that is directly detected or created using a regression model) as its default setting, and a user may select not to display based on his/her preference. In addition, the system displays the longitudinal view of the targeted area of the object, subject, patient (e.g., a targeted vessel), etc. The longitudinal view is created using the acquired intravascular image, and may have multiple patterns. In one example, the longitudinal view may show the 2D cutting plane of the 3D structure that is created by piling and interpolating all the intravascular frames in its pullback direction. Another artificial indicator may be overlaid on the longitudinal view to show the location of the displayed intravascular frame on this view. At least one displaying embodiment example is shown in FIG. 18.

The system also has an ability to check the reliability of coregistration in one or more embodiments. For all options, the anatomical features, such as side branches, that can be detected in both angiography data and the intravascular data can be used. In this case, the reliability value can be the distance between the anatomical features on the angiography data and the coregistration locations of the intravascular image frame that includes the same anatomical features. For Options 1-4, the following method may be used as well. Consider that the intravascular frames that have the indices of the corresponding angiography frame are numbered as $i_{iv}$-th, $j_{iv}$-th, $k_{iv}$-th, $l_{iv}$-th, . . . , and $z_{iv}$-th. The system chooses two intravascular frames that have the indices of the corresponding angiography frame number [for example, $i_{iv}$-th and $k_{iv}$-th frames]. These two frames should be apart at least one frame that has the index of the corresponding angiography frame number [in this example, the $j_{iv}$-th frame is skipped]. Then, the system estimates the coregistration location for each of the intravascular frames that are acquired between the two selected frames, $i_{iv}$-th and $k_{iv}$-th frames. After that, the estimated coregistration location(s) is/are compared to the actual coregistration location(s) that is/are directly detected (and updated) from the corresponding angiography frame [in this example, the comparison is performed for the $j_{iv}$-th frame]. The difference between the actual and the estimated locations is considered as a reliability value. If the reliability value exceeds a certain threshold, an alert may be shown on the monitor or display when the coregistration result is displayed. The threshold may be pre-determined by the system, or may be determined by a user based on his/her preference. An alert may be a text message on the display, and/or may be a graphical output, such as a color-coded indicator (see e.g., the reliability indicator shown in FIG. 18) and an indicator with different line style or different shape.

In one or more embodiments, coregistration feature(s) may be available in any angiography image acquisition option(s), and coregistration may be performed even in a case where a user finishes the intravascular imaging pullback.

In the aforementioned embodiments, in Options 1 through 4, where the image processor obtains at least one angiography image frame acquired during the pullback, the image processor may detect a location of a marker of the catheter in the acquired at least one angiography image, as shown in FIG. 10A. The detected location of the marker may be used to co-register the intravascular images. This process may be referred to as a first algorithm.

In contrast, as shown in Option 5 or Option 6, in a case where the angiography image frame is not acquired during the pullback but acquired before the pullback or before the contrast agent (or a flushing media or agent) reaches the target vessel, co-registration may be performed by using the user inputs by interpolation or extrapolation. This process (es) may be referred to as a second algorithm(s).

Please note that even in the Options 1 through 4, if a frame rate of the angiography frames is not as high as that of intravascular images, based on the co-registration results of some angiography images by the marker detection results, the interpolation or extrapolation may be (or preferably is) performed to co-register the intravascular images that do not have corresponding angiography frames, as shown in FIGS. 12A-12B. This means that, based on the timing of the angiography image frame acquisition, and optionally, the frame rates of the angiography image frames and intravascular images, at least one of the first algorithm and the second algorithm(s) is selected to perform the process for co-registration or co-registration process. In other words, the image processor or other processor may determine whether or not to detect a marker in the angiography image frame and to utilize the detection result, based on the timing. Therefore, the image processor or other processor may reduce the processing time and resources by utilizing the timing information.

In the aforementioned embodiments, regarding the co-registration path generation, the timing information also may be utilized to determine how to generate the path.

In Options 1 through 4, the image processor or other processor may generate the co-registration path based on the location of the marker of the OCT imaging catheter in the angiography image as shown in the FIG. 10D, whereas in Options 5 and 6, the image processor or other processor may generate the co-registration path (or imaging catheter path) by detecting the guidewire or the sheath, as described above.

Please note that, even in Option 1, there may be other ways to generate a co-registration path without using the detected location of the marker. In one way, the image processor or other processor may generate a line along and within the target vessel by applying a segmentation technique or a skeletonization technique to the target vessel, since in Option 1 the target vessel is filled with the contrast agent, which makes it easy for the image processor or other processor to detect the target vessel. In this example, in a case where an angiography image frame is acquired before a contrast agent reaches the target area, a guidewire or a sheath inserted into the target vessel may be detected to co-register the intravascular images, and in a case where an angiography image frame is acquired during the OCT pullback, the target vessel may be detected in the image frame to co-register the intravascular images acquired during the pullback.

Figure 19A:
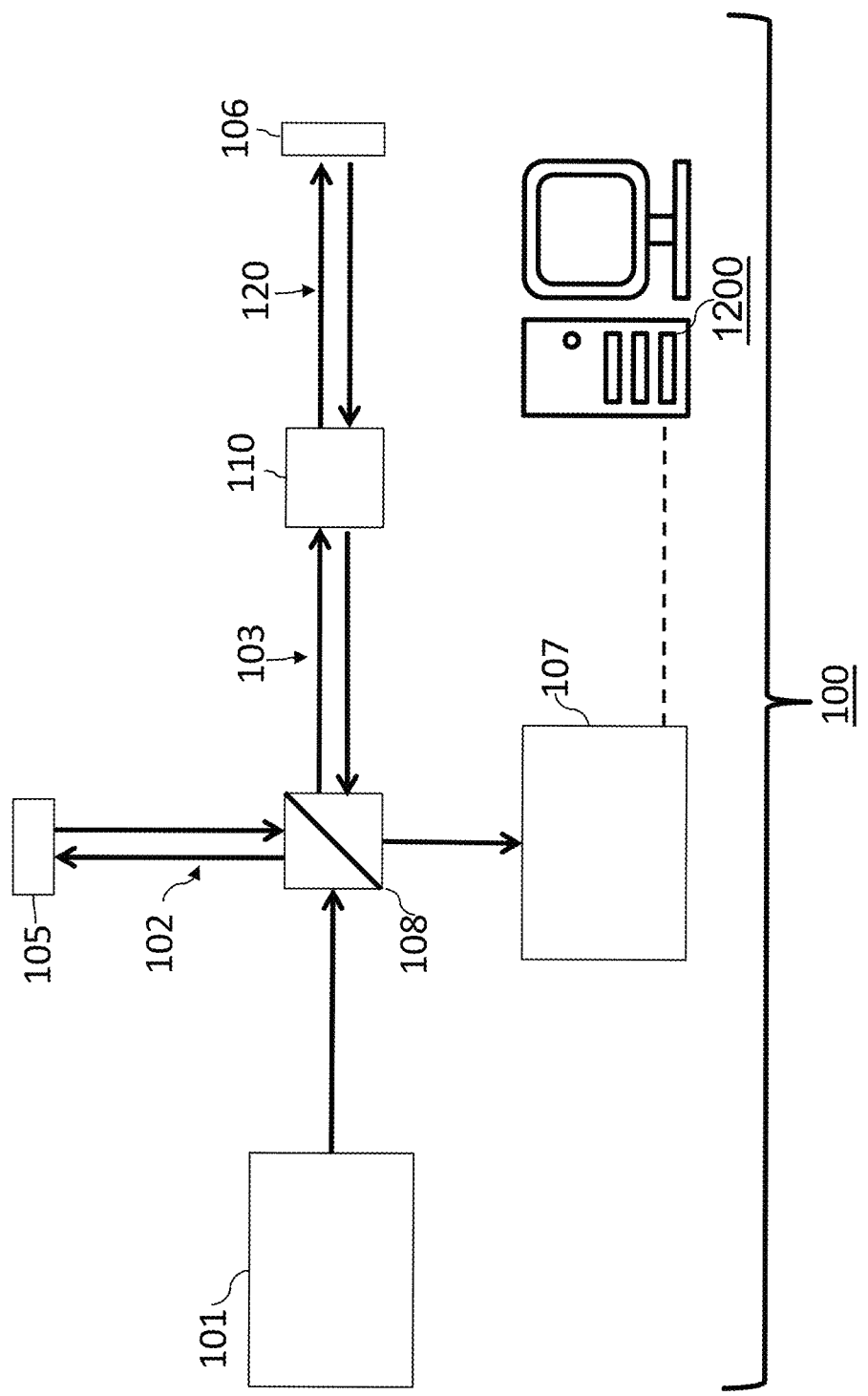
FIG. 19A shows at least one embodiment of an OCT apparatus or system for using coregistration or selecting an appropriate co-registration method in accordance with one or more aspects of the present disclosure.

FIG. 19A shows an OCT system 100 (as referred to herein as "system 100" or "the system 100") which operates to utilize an OCT technique, feature, or function with coregistration or with selection of an appropriate co-registration method applications in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107 (which may be connected to a computer 1200). In one or more embodiments, the system 100 may include a patient interface device or unit ("PIU") no and a catheter 120 (see e.g., embodiment examples of a PIU and a catheter as shown in FIG. 2), and the system 100 may interact with a sample, object, patient (e.g., a blood vessel of a patient), target 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

Figure 19B:
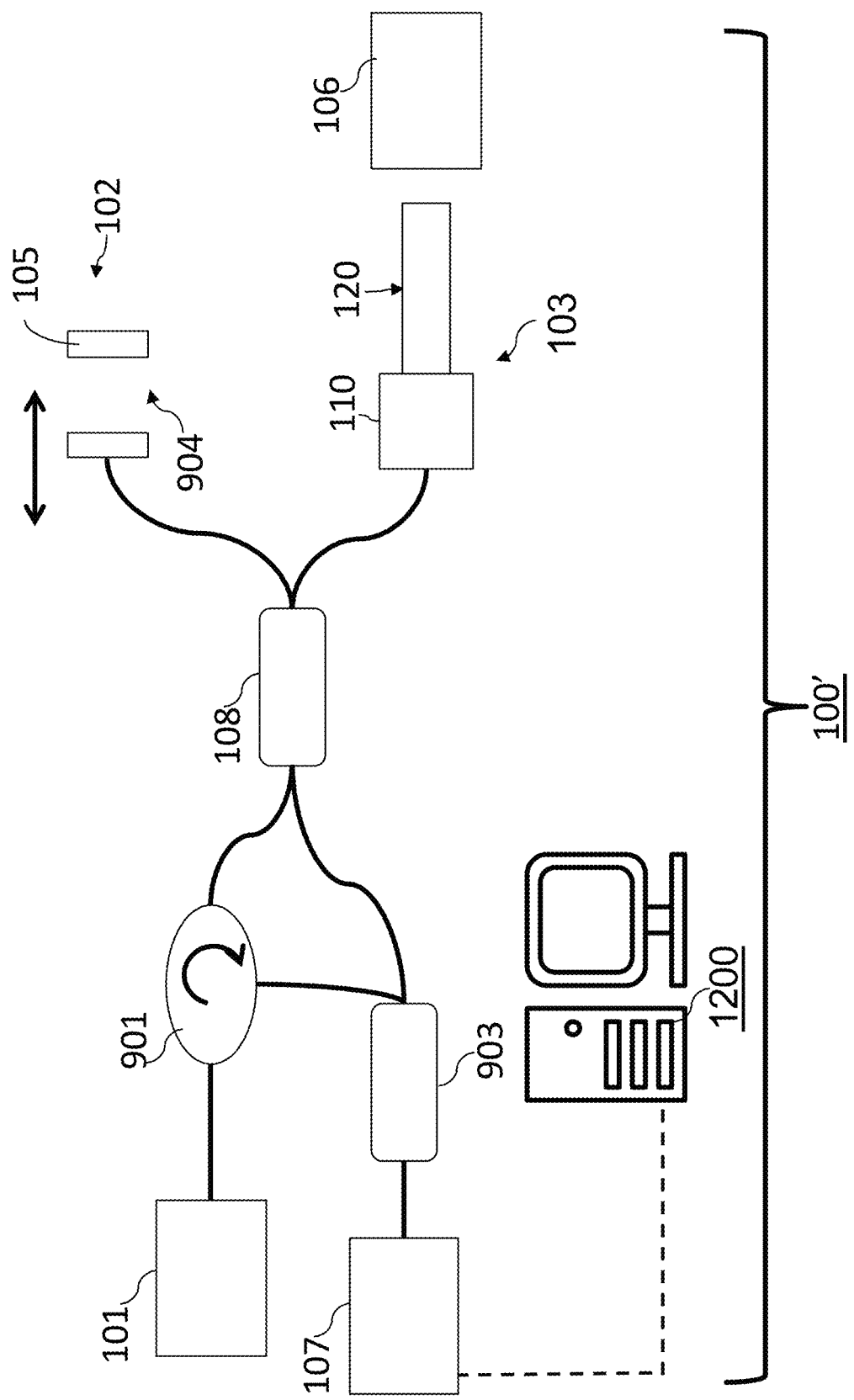
FIG. 19B shows at least another embodiment of an OCT apparatus or system for using coregistration or selecting an appropriate co-registration method in accordance with one or more aspects of the present disclosure.

In accordance with one or more further aspects of the present disclosure, bench top systems may be utilized with the coregistration technique(s) (and/or feature(s) or function(s)/option(s)) and/or selecting an appropriate co-registration method as disclosed herein. FIG. 19B shows an example of a system that can utilize the coregistration technique(s) (and/or feature(s) or function(s)/option(s)) and/or selecting an appropriate co-registration method for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as or similar to the reference mirror or reference reflection 105 shown in FIG. 19A) in the reference arm 102 while a sample beam is reflected or scattered from a sample, target, object, patient (e.g., blood vessel of a patient), etc. 106 in the sample arm 103 (e.g., via the PIU no and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIGS. 19A-19C; also shown in FIG. 21 discussed further below), the computer 1200' (see e.g., FIG. 22 discussed further below), etc.

Figure 19C:
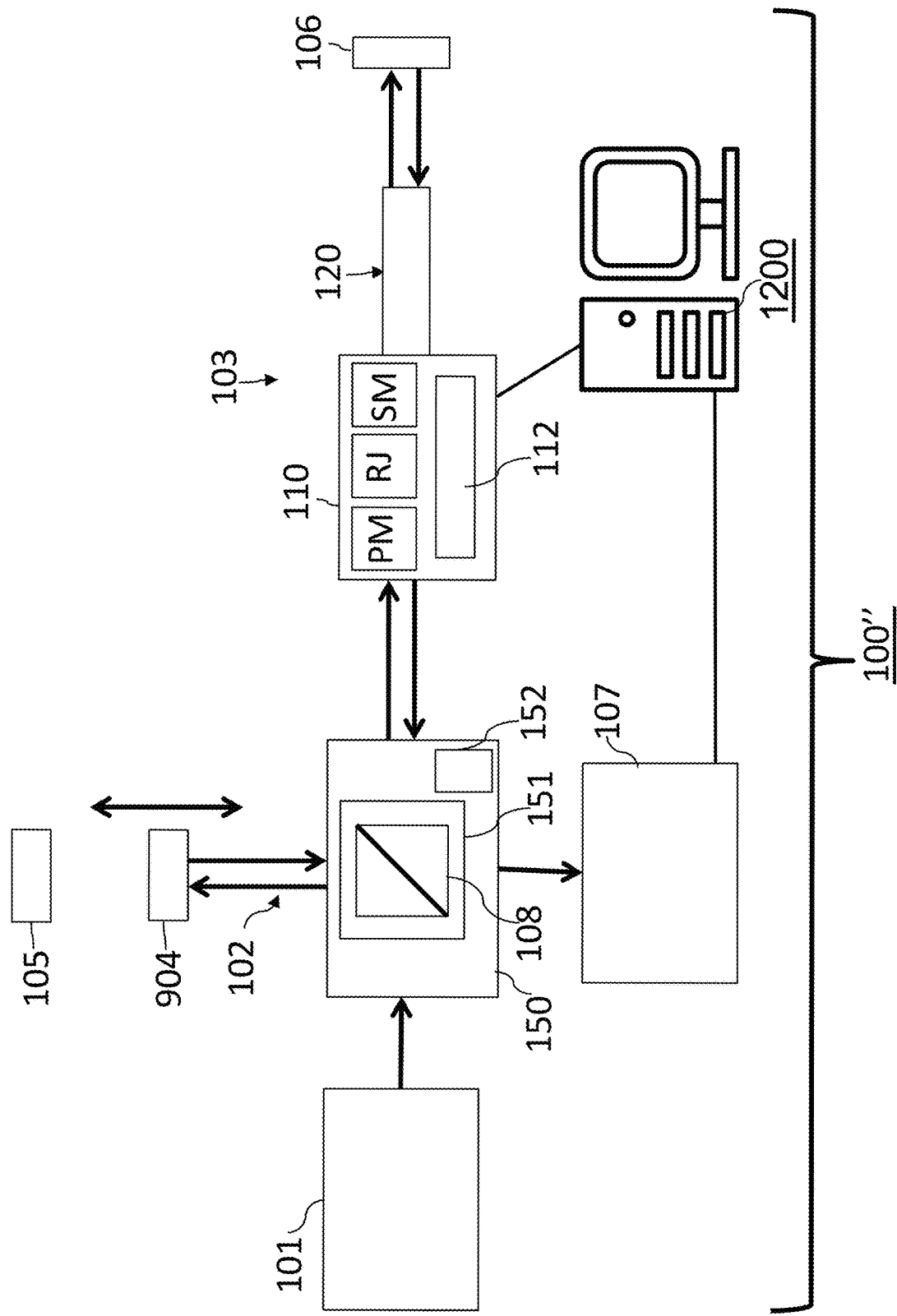
FIG. 19C shows at least a further embodiment of an OCT apparatus or system for using coregistration or selecting an appropriate co-registration method in accordance with one or more aspects of the present disclosure.

In accordance with one or more further aspects of the present disclosure, one or more other systems may be utilized with the coregistration technique(s) (and/or feature(s) or function(s)/option(s)) and/or selecting an appropriate co-registration method as disclosed herein. FIG. 19C shows an example of a system 100" that may utilize the coregistration technique(s) (and/or feature(s) or function(s)/option(s)) and/or selecting an appropriate co-registration method such as for ophthalmic applications. A light from a light source 101 delivers and splits into a reference arm 102 and a sample arm 103 with a deflecting section 108 (e.g., a beamsplitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may go or pass through a length adjustment section 904, which may operate to change the distance of a reference mirror (such as reference mirror or reference reflection 105; also shown in FIG. 19A for example) and is reflected from the reference reflection 105 in the reference arm 102 while a sample beam is reflected or scattered from a sample, target, object, patient (e.g., blood vessel of a patient), etc. 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIGS. 19A-19C; also shown in FIG. 21 discussed further below), the computer 1200' (see e.g., FIG. 22 discussed further below), etc. In one or more embodiments, the sample arm 103 includes the PIU no and the catheter 120 so that the sample beam is reflected or scattered from the sample, target, object, patient (e.g., blood vessel of a patient), etc. 106 as discussed herein. In one or more embodiments, the PIU no may include one or more motors to control the pullback operation of the catheter 120 (or one or more components thereof) and/or to control the rotation or spin of the catheter 120 (or one or more components thereof). For example, the PIU no may include a pullback motor (PM) and a spin motor (SM), and/or may include a motion control unit 112 that operates to perform the pullback and/or rotation features using the pullback motor PM and/or the spin motor SM. As discussed herein, the PIU no may include a rotary junction (e.g., rotary junction RJ as shown in FIG. 19C). The rotary junction RJ may be connected to the spin motor SM so that the catheter 120 may obtain one or more views or images of the sample, target, object, patient (e.g., blood vessel of a patient), etc. 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU no, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Preferably, in one or more embodiments including the deflecting or deflected section 108 (best seen in FIGS. 19A-19C), the deflected section 108 operates to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc.

While not limited to such arrangements, configurations, devices or systems, one or more embodiments of the methods discussed herein may be used with an apparatus or system as aforementioned, such as, but not limited to, for example, the system 100, the system 100', the system 100", the system of FIG. 2, any other system discussed herein, etc. In one or more embodiments, one user may perform the method(s) discussed herein. In one or more embodiments, one or more users may perform the method(s) discussed herein.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, registration, coregistration, selecting an appropriate co-registration method and/or any other method discussed herein. The light source 101 may be fiber coupled or may be free space coupled to the other components of the apparatus and/or system 100, 100', 100", the system of FIG. 2, or any other embodiment discussed herein.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC).

Figure 20:
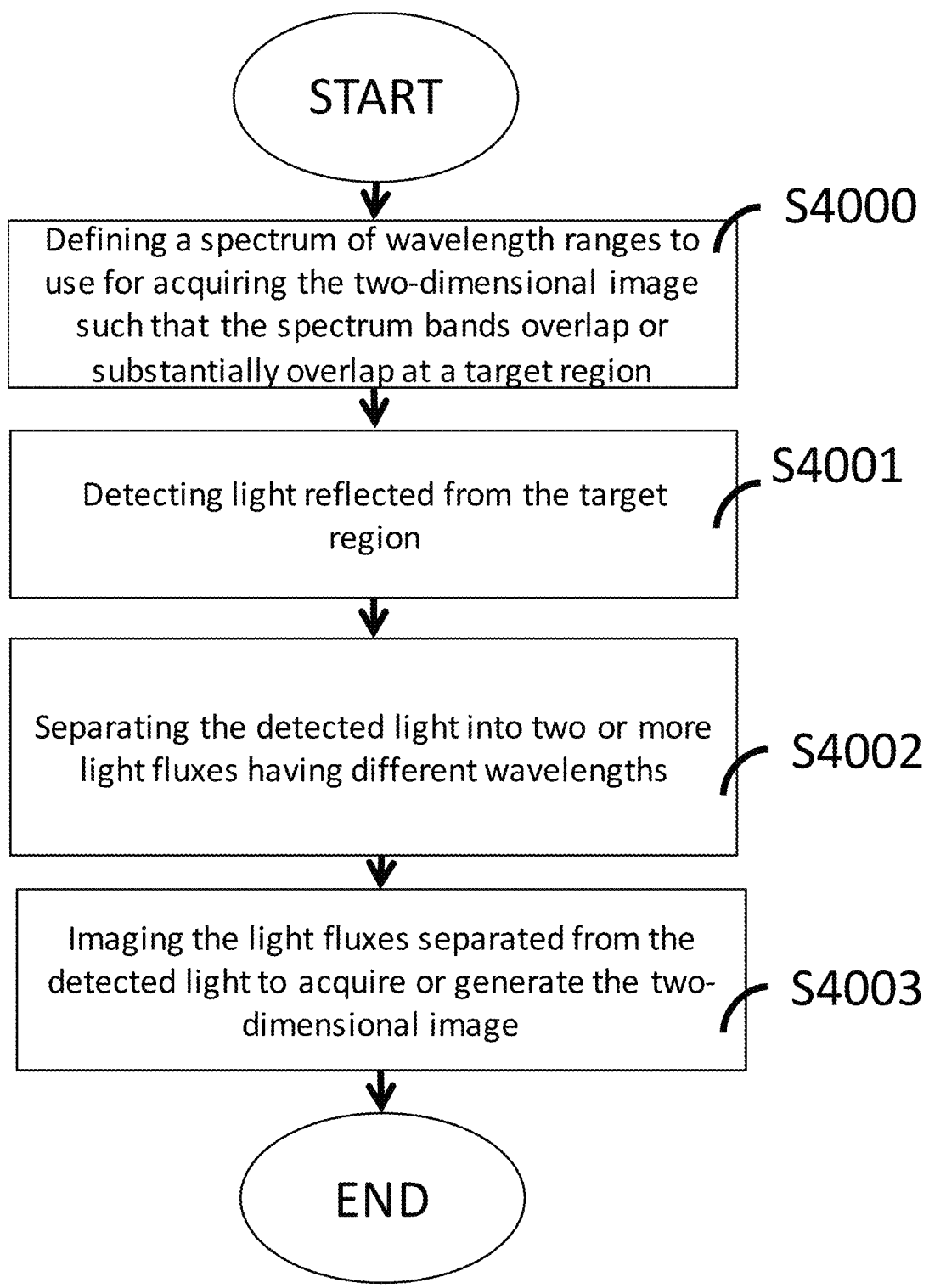
FIG. 20 is a flow diagram showing a method of performing an imaging feature, function or technique in accordance with one or more aspects of the present disclosure.

In accordance with one or more aspects of the present disclosure, one or more methods for performing imaging are provided herein. FIG. 20 illustrates a flow chart of at least one embodiment of a method for performing imaging. Preferably, the method(s) may include one or more of the following: (i) defining a spectrum of wavelength ranges to use for acquiring the image such that the spectrum bands overlap or substantially overlap on a sample or target (see step S4000 in FIG. 20); (ii) detecting light reflected from the target region (see step S4001 in FIG. 20); (iii) separating the detected light into two or more light fluxes having different wavelengths (see step S4002 in FIG. 20); and imaging the light fluxes separated from the detected light to acquire or generate the black and white and/or color image (see step S4003 in FIG. 20). One or more methods may further include at least one of: using a probe grating to generate the spectrum bands that overlap or substantially overlap on the target region; and optimizing the probe grating so that a diffraction efficiency is high within the wavelength ranges. In one or more embodiments, an imaging probe may be connected to one or more systems (e.g., the system 100, the system 100', the system 100", the system of FIG. 2, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

The one or more detectors 107 may transmit the digital or analog signals to a processor or a computer such as, but not limited to, an image processor, a processor or computer 1200, 1200' (see e.g., FIGS. 19A-19C and 21-22), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the system of FIG. 2, the computer 1200, the computer 1200', the image processor, may also include one or more components further discussed herein below (see e.g., FIGS. 21-22).

In at least one embodiment, a console or computer 1200, 1200' operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 19A-19C and FIG. 21 and/or the console 1200' of FIG. 22 as further discussed below). In one or more embodiments, the MCU 112 or the motor M operates to change a speed of a motor of the RJ and/or of the RJ. The motor may be a stepping or a DC servo motor to control the speed and increase position accuracy.

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", and/or the detector(s) 107 thereof, and/or from the system of FIG. 2, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems, such as, but not limited to, the system 100, the system 100', the system 100", or any other system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 112, the RJ, the at least one detector 107, and/or one or more other elements of the system 100 may operate in the same or similar fashion to those like-numbered elements of one or more other systems, such as, but not limited to, the system of FIG. 2, the system 100', the system 100", or any other system discussed herein. Those skilled in the art will appreciate that alternative embodiments of the system of FIG. 2, the system 100', the system 100", any other system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 19A and one or more embodiments shown in any of FIGS. 2 and 19B-19C, for example, as discussed herein, there are similarities. Likewise, while the console or computer 1200 may be used in one or more systems (e.g., the system 100, the system 100', the system 100", the system of FIG. 2, or any other system discussed herein, etc.), one or more other consoles or computers, such as the console or computer 1200', may be used additionally or alternatively.

There are many ways to compute intensity, viscosity, resolution (including increasing resolution of one or more images), registration, coregistration, selecting an appropriate co-registration method or any other measurement discussed herein, digital as well as analog. In at least one embodiment, a computer, such as the console or computer 1200, 1200', may be dedicated to control and monitor the imaging (e.g., OCT, IVUS, multimodal OCT, etc.) devices, systems, methods and/or storage mediums described herein.

The electric signals used for imaging may be sent to one or more processors, such as, but not limited to, a computer 1200 (see e.g., FIGS. 19A-19C and 21), a computer 1200' (see e.g., FIG. 22), etc. as discussed further below, via cable(s) or wire(s), such as, but not limited to, the cable(s) or wire(s) 113 (see FIG. 21).

Figure 21:
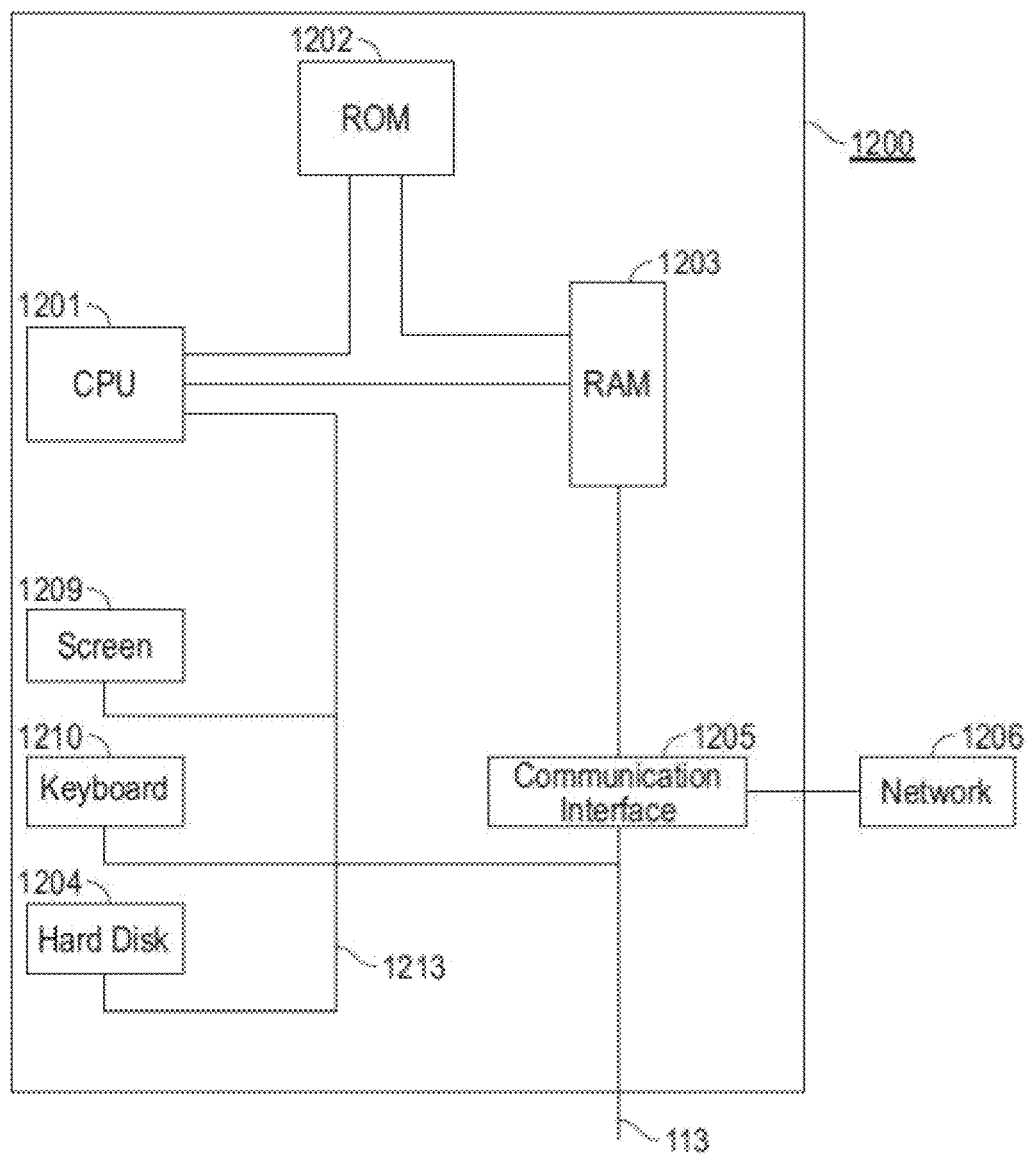
FIG. 21 shows a schematic diagram of an embodiment of a computer that may be used with one or more embodiments of an imaging apparatus or system one or more methods discussed herein in accordance with one or more aspects of the present disclosure.

Various components of a computer system 1200 are provided in FIG. 21. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., including but not limited to, being connected to the console, the probe, the imaging apparatus or system, any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, an apparatus or system using one or more coregistration technique(s) (and/or feature(s) or function(s)/option(s)) and/or selecting an appropriate coregistration method as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or sample characterization, diagnosis, evaluation and/or imaging. The system 1200 may further include one or more processors connected via a network connection (e.g., via network 1206). The CPU 1201 and any additional processor being used by the system 1200 may be located in the same telecom network or in different telecom networks (e.g., performing feature(s), function(s), technique(s), method(s), etc. discussed herein may be controlled remotely).

Figure 22:
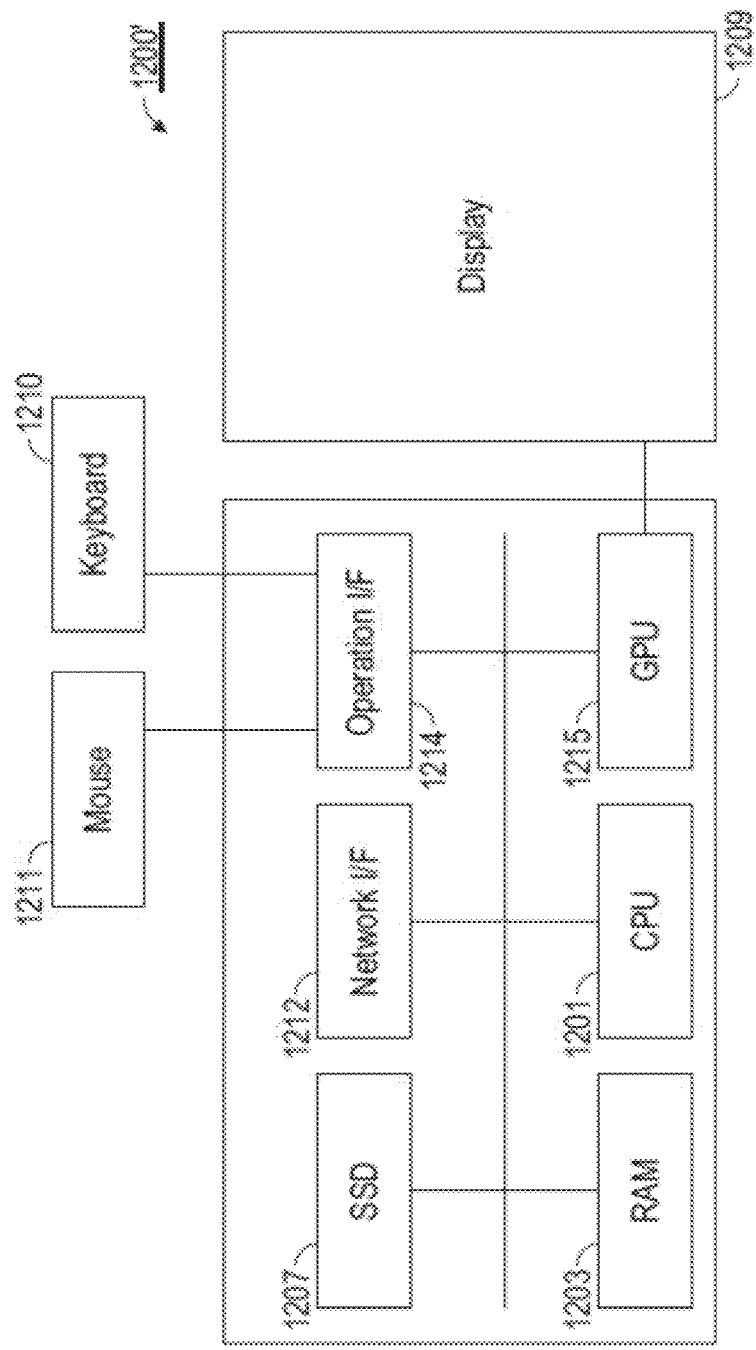
FIG. 22 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include a light source, a spectrometer, the communication interface of the computer 1200 may connect to other components discussed herein via line 113 (as diagrammatically shown in FIG. 21), a microphone, a communication cable and a network (either wired or wireless), a keyboard 1210, a mouse (see e.g., the mouse 1211 as shown in FIG. 22), a touch screen or screen 1209, a light pen and so on. The Monitor interface or screen 1209 provides communication interfaces thereto.

Any methods and/or data of the present disclosure, such as the methods for performing tissue or sample characterization, diagnosis, examination and/or imaging (including, but not limited to, increasing image resolution, performing coregistration, selecting an appropriate co-registration method (and/or option(s) or feature(s)), etc.), for example, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 22), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 21. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 21) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 22. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 21). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 1200, 1200', may communicate with an MCU, an interferometer, a spectrometer, a detector, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7, 551,293; 7,796,270; 7,859,679; 7,872,759; 7,889,348; 8,045,177; 8,145,018; 8,289,522; 8,838,213; 8,928,889; 9,254,089; 9,295,391 to Tearney et al.; U.S. Pat. Nos. 9,415,550; 9,557,154 as well as the disclosures in Patent Application Publication Nos. WO2015/116951; WO2015/116939; WO2017/117203; WO2017/024145; WO2017/165511A1; in U.S. Pat. No. 9,332,942; in U.S. Patent Publication Nos. 2012/0101374; 2016/0349417; US2017/0035281; 2017/167861; 2017/0168232; 2017/0176736; 2017/0290492; 2017/0322079; and in U.S. Non-Provisional patent application Ser. No. 15/418,329 filed Jan. 27, 2017 and published as U.S. Pat. Pub. No. 2018/0017778, each of which patents, patent publications and application(s) are incorporated by reference herein in their entireties.

Similarly, the present disclosure and/or one or more components of devices, systems and storage mediums, and/ or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, and 2016/0228097, and WO 2016/144878, each of which patents and patent publications are incorporated by reference herein in their entireties.

Similarly, the present disclosure and/or one or more components of devices, systems and storage mediums, and/ or methods, thereof also may be used in conjunction with imaging technologies and methods (e.g., for coregistration), such as, but not limited to, apparatuses, assemblies, systems, methods and/or storage mediums disclosed in at least, but not limited to: U.S. Pat. App. No. 62/474,248, filed on Mar. 21, 2017, the disclosure of which is incorporated by reference herein in its entirety; U.S. patent application Ser. No. 15/923,956, filed on Mar. 16, 2018, the disclosure of which is incorporated by reference herein in its entirety; U.S. Pat. App. No. 62/537,204, filed on Jul. 26, 2017, the disclosure of which is incorporated by reference herein in its entirety; U.S. patent application Ser. No. 16/044,881, filed on Jul. 25, 2018, the disclosure of which is incorporated by reference herein in its entirety; U.S. Pat. App. No. 62/680,780, filed on Jun. 5, 2018, the disclosure of which is incorporated by reference herein in its entirety; U.S. patent application Ser. No. 16/044,931, filed on Jul. 25, 2018, the disclosure of which is incorporated by reference herein in its entirety; PCT/US2018/043743, filed on Jul. 25, 2018, the disclosure of which is incorporated by reference herein in its entirety; and PCT/US2018/043756, filed on Jul. 25, 2018, the disclosure of which is incorporated by reference herein in its entirety.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A method for performing co-registration between one or more image frames and one or more images, the method comprising:

acquiring, obtaining, or receiving one or more images acquired in one or more imaging procedures in which an imaging probe or catheter is inserted into a predetermined target area of an object or subject;

obtaining or receiving one or more images or image frames to be co-registered with the one or more images;

obtaining, receiving, or determining timing information indicating a timing when the one or more images or image frames are acquired with respect to the one or more imaging procedures;

determining a process for co-registration between the one or more images and the one or more images or image frames, based on the obtained, received, or determined timing information;

applying the determined process for co-registration to the obtained images and the obtained one or more images or image frames;

selecting an image or image frame from one or more first images or image frames including a flushing media or agent and/or a contrast media and selecting an image or image frame from one or more second images or image frames not including a flushing media or agent and/or a contrast media having identical cardiac phase signals; and in a case where it is determined that a detected path of the imaging probe or catheter of the image or image frame from the one or more second images or image frames is not located within a contour of the predetermined target area of the image or image frame from the one or more first images or image frames, selecting another image or image frame from the one or more second images or image frames at an identical cardiac phase signal, overlaying the image or image frame from the one or more first images or image frames with the another image or image frame from the one or more second images or image frames to determine whether the detected path of the imaging probe or catheter of the another image or image frame from the one or more second images or image frames is located within the predetermined target area contour of the image or image frame from the one or more first images or image frames, and determining whether a marker associated with or detected in the image or image frame from the one or more first images or image frames is located on the detected path of the imaging probe or catheter of the another image or image frame from the one or more second images or image frames in response to a determination that the detected path of the imaging probe or catheter of the another image or image frame from the one or more second images or image frames is located within the predetermined target area contour of the image or image frame from the one or more first images or image frames.

2. The method of claim 1, wherein one or more of the following:
(i) the one or more first images or image frames and/or the one or more second images or image frames are one or more angiography images or image frames, the one or more images are one or more intravascular images, and the one or more imaging procedures are one or more intravascular imaging procedures;
(ii) the process for co-registration is selected and applied such that co-registration and/or at least one co-registration algorithm is available in one or more image acquisition options;
(iii) the co-registration is performed in a case where imaging by one or more imaging modalities is performed during a partial or an entire intravascular imaging pullback, is performed before pullback has occurred, and/or is performed after the intravascular imaging pullback is or has been finished; and/or
(iv) the one or more image acquisition options are one or more angiography image acquisition options, and the one or more imaging modalities is an angiography modality.

3. The method of claim 1, wherein one or more of the following:
(i) the predetermined target area of the object or the subject is a blood vessel; and/or
(ii) the predetermined target area of the object or the subject is a blood vessel, and the blood vessel is flushed with a flushing media or agent, and then pullback of the imaging probe or catheter is performed to acquire the one or more images.

4. The method of claim 1, wherein the timing information indicates one or more of the following:
(i) whether the one or more first images or image frames and/or the one or more second images or image frames are acquired during an imaging pullback, before the pullback, or after the pullback;
(ii) whether or not the one or more first images or image frames and/or the one or more second images or image frames are acquired when the predetermined target area of the subject or object is flushed with a flushing media or agent; and/or
(iii) whether or not the one or more first images or image frames and/or the one or more second images or image frames are acquired during an entire period of the pullback.

5. The method of claim 1, wherein in the determining of the process for co-registration, it is determined that at least one of a first algorithm and a second algorithm is selected for the process for co-registration.

6. The method of claim 5, wherein, in the first algorithm, a location of a marker of the imaging probe or catheter in one of the first images or image frames and/or in one of the second images or image frames is detected to coregister the one of the first images or image frames and/or of the second images or image frames with the one or more images acquired in one or more imaging procedures.

7. The method of claim 5, wherein, in the second algorithm, a predetermined registration information between one of the one or more images acquired in one or more imaging procedures and one of the first images or image frames and/or of the second images or image frames is obtained to coregister the others of the one or more images with one of the first images or image frames and/or of the second images or image frames by interpolation or extrapolation.

8. The method of claim 1, wherein, in the process for co-registration, in a case where an image or image frame of the first images or image frames and/or of the second images or image frames is acquired before a flushing media or agent reaches the target area, a guidewire or a sheath inserted into the target area is detected to generate a co-registration path.

9. The method of claim 1, wherein, in the process for co-registration, in a case where an image or image frame of the first images or image frames and/or of the second images or image frames is acquired during one or more imaging procedures, a location of a marker of the imaging probe or catheter is detected in the image or image frame to coregister the one or more images acquired in the one or more imaging procedures.

10. The method of claim 1, wherein, in the process for co-registration,
in a case where an image or image frame of the first images or image frames and/or of the second images or image frames is acquired before a flushing media or agent reaches the target area, a guidewire or a sheath inserted into the target area is detected to co-register the one or more images acquired in one or more imaging procedures, and
in a case where an image or image frame of the first images or image frames and/or of the second images or image frames is acquired during the one or more imaging procedures, the target area is detected in the image or image frame to co-register the one or more images acquired in the one or more imaging procedures.

11. The method of claim 1, wherein:
(i) in a case where the one or more first images or image frames and/or the one or more second images or image frames are acquired, obtained, or received during an imaging pullback, the determined process includes determining a position in one of the one or more first and/or second images or image frames where at least one image is acquired, obtained, or received;
(ii) in a case where the one or more first and/or second images or image frames are acquired during the pullback but not during an entire period of the pullback, the determined process includes interpolating a position of at least one of the one or more images using information regarding a speed of the pullback; and (iii) in a case where the one or more first and/or second images or image frames are acquired before or after the pullback, the determined process includes obtaining the starting and the ending location of the pullback from a user and interpolating a position of at least one of the one or more images using information regarding a speed of the pullback.

12. The method of claim 1, further comprising:
storing a path of the imaging probe or catheter of the image or image frame from the one or more second images or image frames as a co-registration path on the image or image frame from the one or more first images or image frames in response to a determination that a marker associated with the image or image frame from the one or more first images or image frames is located on the path of the imaging probe or catheter of the image or image frame from the one or more second image frames.

13. The method of claim 1, wherein the acquiring, obtaining, or receiving step, the obtaining or receiving step, the obtaining, receiving, or determining timing information step, the determining step, and the applying step are repeated for each image or image frame from the one or more first images or image frames until a last image or image frame from the first images or image frames.

14. The method of claim 1, further comprising:
in a case where no other image or image frame from the one or more second images or image frames at the identical cardiac phase signal exists, then the selecting step, the overlaying step, and the determining step are repeated for another image or image frame from the first images or image frames.

15. The method of claim 14, wherein in a case where it is determined in the determining step that the marker associated with the image or image frame from the one or more first images or image frames is not located on the detected path of the imaging probe or catheter of the another image or image frame from the one or more second images or image frames, the determining step determines whether the marker associated with the image or image frame from the one or more first images or image frames is located within a predetermined distance from the detected path of the imaging probe or catheter of the another image or image frame from the one or more second images or image frames; and wherein when the marker associated with the image or image frame from the one or more first images or image frames is located within the predetermined distance from the detected path of the imaging probe or catheter of the another image or image frame from the second images or image frames, a location on the detected path of the imaging probe or catheter of the another image or image frame from the second images or image frames that is closest to the marker location is stored as an updated marker associated with the image or image frame from the one or more first images or image frames.

16. The method of claim 1, further comprising:
importing intravascular imaging data including a plurality of intravascular images or image frames acquired simultaneously to or with angiography data;
selecting an angiography image or image frame with a co-registration path;

determining at least two intravascular images or image frames from the one or more images or image frames that correspond to the selected angiography image frame based on a timestamp;
calculating an intravascular image or image frame acquisition location on the co-registration path based on the at least two intravascular images or image frames; and
displaying the angiography image or image frame with the co-registration path and an indicator representing the intravascular image or image frame acquisition location.

17. The method of claim 1, further comprising:
detecting a contour of the predetermined target area and a marker for angiography images or image frames including a flushing media or agent and/or a contrast media in a targeted area and saving the predetermined target area contour, the marker, and the associated cardiac phase signal for the angiography images or image frames including a flushing media or agent and/or a contrast media in the targeted area;
searching for one or multiple dark points in the angiography images or image frames including a flushing media or agent and/or a contrast media; and
tracking each of the searched one or multiple dark points for each angiography image or image frame including a flushing media or agent and/or a contrast media and determining the marker or a radiopaque marker based on a direction determined by the tracking.

18. An imaging apparatus for performing co-registration and/or selecting a co-registration algorithm, the imaging apparatus comprising:
one or more processors that operate to:
acquire, obtain, or receive one or more images acquired in one or more imaging procedures in which an imaging probe or catheter is inserted into a predetermined target area of an object or subject;
obtain or receive one or more images or image frames to be co-registered with the one or more images;
obtain, receive, or determine timing information indicating a timing when the one or more images or image frames are acquired with respect to the one or more imaging procedures;
determine a process for co-registration between the one or more images and the one or more images or image frames, based on the obtained, received, or determined timing information;
apply the determined process for co-registration to the obtained images and the obtained one or more images or image frames;
select an image or image frame from one or more first images or image frames including a flushing media or agent and/or a contrast media and selecting an image or image frame from one or more second images or image frames not including a flushing media or agent and/or a contrast media having identical cardiac phase signals; and
in a case where it is determined that a detected path of the imaging probe or catheter of the image or image frame from the one or more second images or image frames is not located within a contour of the predetermined target area of the image or image frame from the one or more first images or image frames, select another image or image frame from the one or more second images or image frames at an identical cardiac phase signal, overlay the image or image frame from the one or more first images or image frames with the another image or image frame from the one or more second images or image frames to determine whether the detected path of the imaging probe or catheter of the another image or image frame from the one or more second images or image frames is located within the predetermined target area contour of the image or image frame from the one or more first images or image frames, and determine whether a marker associated with or detected in the image or image frame from the one or more first images or image frames is located on the detected path of the imaging probe or catheter of the another image or image frame from the one or more second images or image frames in response to a determination that the detected path of the imaging probe or catheter of the another image or image frame from the one or more second images or image frames is located within the predetermined target area contour of the image or image frame from the one or more first images or image frames.

19. A method for performing co-registration between first image data and second image data, the method comprising:
importing first image data including a plurality of images or image frames acquired during a pullback of an imaging catheter including a radiopaque marker, and importing second imaging data including a plurality of images or image frames acquired simultaneously to the first image data, wherein the images or image frames of the first image data include a flushing media or agent and/or a contrast media in a targeted region;
detecting a marker for the images or image frames of the first image data, the images or image frames including a flushing media or agent and/or a contrast media in the targeted region;
generating a path based upon the detected marker from the images or image frames of the first image data, the images or image frames including a flushing media or agent and/or a contrast media;
calculating an acquisition location of at least one of the images or image frames of the second image data, in at least one of the image frames of the first image data, using the generated path;
selecting an image or image frame from one or more first images or image frames of the first image data and selecting an image or image frame from one or more second images or image frames not including a flushing media or agent and/or a contrast media having identical cardiac phase signals; and
in a case where it is determined that a detected path of the imaging probe or catheter of the image or image frame from the one or more second images or image frames is not located within a contour of the predetermined target area of the image or image frame from the one or more first images or image frames, selecting another image or image frame from the one or more second images or image frames at an identical cardiac phase signal, overlaying the image or image frame from the one or more first images or image frames with the another image or image frame from the one or more second images or image frames to determine whether the detected path of the imaging probe or catheter of the another image or image frame from the one or more second images or image frames is located within the predetermined target area contour of the image or image frame from the one or more first images or image frames, and determining whether a marker associated with or detected in the image or image frame from the one or more first images or image frames is located on the detected path of the imaging probe or catheter of the another image or image frame from the one or more second images or image frames in response to a determination that the detected path of the imaging probe or catheter of the another image or image frame from the one or more second images or image frames is located within the predetermined target area contour of the image or image frame from the one or more first images or image frames.

20. The method of claim 19, wherein one or more of the following:
(i) the first image data is angiography data, the second image data is intravascular image data, the plurality of images or image frames of the first image data are angiography images or image frames, and the plurality of images or image frames of the second image data are intravascular images or image frames;
(ii) in the generating step, the path is a regression line generated based upon the detected marker, and the regression line is stored as a co-registration path on the selected angiography image or image frame;
(iii) in a case where it is determined that the marker associated with the selected angiography image or image frame is not on the generated path, then a location on the generated path that is closest to the marker associated with the selected angiography image or image frame is stored as a new marker associated with the selected angiography image or image frame;
(iv) an angiography image or image frame with the generated path is selected;
(v) at least two intravascular images or image frames from the plurality of intravascular images or image frames that correspond to the selected angiography image or image frame are determined based on a timestamp;
(vi) an intravascular image or image frame acquisition location on the generated path is calculated based on the at least two intravascular images or image frames; and
(vii) the angiography image or image frame with the generated path and an indicator representing the intravascular image or image frame acquisition location is displayed.

21. The method of claim 1, further comprising obtaining or receiving view information indicating whether the one or more images or image frames have a single view or multiple views.

22. The method of claim 18, wherein one or more of the following:
(i) the one or more images or image frames are one or more angiography images or image frames, the one or more images are one or more intravascular images, and the one or more imaging procedures are one or more intravascular imaging procedures;
(ii) the process for co-registration is selected and applied such that co-registration and/or at least one co-registration algorithm is available in one or more image acquisition options;
(iii) the co-registration is performed in a case where imaging by one or more imaging modalities is performed during a partial or an entire intravascular imaging pullback, is performed before pullback has occurred, and/or is performed after the intravascular imaging pullback is or has been finished; and/or
(iv) the one or more image acquisition options are one or more angiography image acquisition options, and the one or more imaging modalities is an angiography modality.

23. The method of claim 18, further comprising obtaining or receiving view information indicating whether the one or more images or image frames have a single view or multiple views.

24. The method of claim 1, further comprising:
storing a path of the imaging probe or catheter of the image or image frame from the one or more second images or image frames as a co-registration path on the image or image frame from the one or more first images or image frames in response to a determination that a marker associated with the image or image frame from the one or more first images or image frames is located on the path of the imaging probe or catheter of the image or image frame from the one or more second image frames;

in a case where it is determined in the determining step that the marker associated with the image or image frame from the one or more first images or image frames is not located on the detected path of the imaging probe or catheter of the another image or image frame from the one or more second images or image frames, determining whether the marker associated with the image or image frame from the one or more first images or image frames is located within a predetermined distance from the detected path of the imaging probe or catheter of the another image or image frame from the one or more second images or image frames;

in a case where the marker associated with the image or image frame from the one or more first images or image frames is located within the predetermined distance from the detected path of the imaging probe or catheter of the another image or image frame from the second images or image frames, storing a location on the detected path of the imaging probe or catheter of the another image or image frame from the second images or image frames that is closest to the marker location as an updated marker associated with the image or image frame from the one or more first images or image frames; and in a case where the marker associated with the image or image frame from the one or more first images or image frames is not located within the predetermined distance from the detected path of the imaging probe or catheter of the another image or image frame from the second images or image frames and in a case where no other image or image frame from the one or more second images or image frames at the identical cardiac phase signal exists, repeating, for another image or image frame from the first images or image frames, the selecting step, the overlaying step, the determining whether the marker associated with or detected in the image or image frame from the one or more first images or image frames is located on the detected path step, and the storing path step or the determining whether the marker is located within the predetermined distance step and/or the storing the location step, wherein the acquiring, obtaining, or receiving step, the obtaining or receiving step, the obtaining, receiving, or determining timing information step, the determining the process step, the applying the determined process step, the selecting step, the overlaying step, and at least the determining whether the marker associated with or detected in the image or image frame from the one or more first images or image frames is located on the detected path step, and the storing path step or the determining whether the marker is located within the predetermined distance step and/or the storing the location step, are repeated for each image or image frame from the one or more first images or image frames until a last image or image frame from the first images or image frames.

25. The method of claim 24, wherein one or more of the following:
(i) in a case where the marker associated with the image or image frame from the one or more first images or image frames is not located within the predetermined distance from the detected path of the imaging probe or catheter of the another image or image frame from the second images or image frames and in a case where no other image or image frame from the one or more second images or image frames at the identical cardiac phase signal exists for all images or image frames from the first images or image frames, then the determined process for co-registration is ended; and/or
(ii) a message is displayed indicating that the determined process for co-registration has ended or cannot be further performed.

26. The imaging apparatus of claim 18, wherein the one or more processors further operate to:
store a path of the imaging probe or catheter of the image or image frame from the one or more second images or image frames as a co-registration path on the image or image frame from the one or more first images or image frames in response to a determination that a marker associated with the image or image frame from the one or more first images or image frames is located on the path of the imaging probe or catheter of the image or image frame from the one or more second image frames;

in a case where it is determined that the marker associated with the image or image frame from the one or more first images or image frames is not located on the detected path of the imaging probe or catheter of the another image or image frame from the one or more second images or image frames, determine whether the marker associated with the image or image frame from the one or more first images or image frames is located within a predetermined distance from the detected path of the imaging probe or catheter of the another image or image frame from the one or more second images or image frames;

in a case where the marker associated with the image or image frame from the one or more first images or image frames is located within the predetermined distance from the detected path of the imaging probe or catheter of the another image or image frame from the second images or image frames, store a location on the detected path of the imaging probe or catheter of the another image or image frame from the second images or image frames that is closest to the marker location as an updated marker associated with the image or image frame from the one or more first images or image frames; and in a case where the marker associated with the image or image frame from the one or more first images or image frames is not located within the predetermined distance from the detected path of the imaging probe or catheter of the another image or image frame from the second images or image frames and in a case where no other image or image frame from the one or more second images or image frames at the identical cardiac phase signal exists, repeat, for another image or image frame from the first images or image frames, the select, the overlay, the determination whether the marker associated with or detected in the image or image frame from the one or more first images or image frames is located on the detected path, and the storage of the path or the determination whether the marker is located within the predetermined distance and/or the storage of the location, wherein the one or more processors further operate to repeat, for each image or image frame from the one or more first images or image frames until a last image or image frame from the first images or image frames: the acquiring, obtaining, or receiving the one or more images acquired in one or more imaging procedures, the obtaining or receiving the one or more images or image frames, the obtaining, receiving, or determining the timing information, the determining the process, the applying the determined process, the selecting, the overlaying, and at least the determining whether the marker associated with or detected in the image or image frame from the one or more first images or image frames is located on the detected path, and the storing path or the determining whether the marker is located within the predetermined distance and/or the storing the location.

27. The imaging apparatus of claim 26, wherein the one or more processors further operate to one or more of the following:

(i) in a case where the marker associated with the image or image frame from the one or more first images or image frames is not located within the predetermined distance from the detected path of the imaging probe or catheter of the another image or image frame from the second images or image frames and in a case where no other image or image frame from the one or more second images or image frames at the identical cardiac phase signal exists for all images or image frames from the first images or image frames, end the determined process for co-registration; and/or (ii) display a message indicating that the determined process for co-registration has ended or cannot be further performed.

* * * * *